United States Patent

Kirsten et al.

[11] Patent Number: 5,091,529
[45] Date of Patent: Feb. 25, 1992

[54] HERBICIDAL SUBSTITUTED SULPHONYLAMINOAZOLES

[75] Inventors: Rolf Kirsten, Monheim; Joachim Kluth, Langenfeld; Christa Fest, Wuppertal; Ernst Gesing, Erkrath-Hochdahl; Klaus-Helmut Müller, Duesseldorf; Hans-Jochem Riebel; Peter Babczinski, both of Wuppertal; Otto Schallner, Monheim; Hans-Joachim Santel, Leverkusen; Robert R. Schmidt, Bergisch Gladbach; Harry Strang, Duesseldorf, all of Fed. Rep. of Germany

[73] Assignee: Bayer Aktiengesellschaft, Leverkusen, Fed. Rep. of Germany

[21] Appl. No.: 652,347

[22] Filed: Jan. 7, 1991

Related U.S. Application Data

[62] Division of Ser. No. 504,442, Apr. 3, 1990, Pat. No. 5,012,082, which is a division of Ser. No. 317,219, Feb. 28, 1989, Pat. No. 4,941,912.

Foreign Application Priority Data

Mar. 4, 1988 [DE] Fed. Rep. of Germany ....... 3807034
Jul. 29, 1988 [DE] Fed. Rep. of Germany ....... 3825867

[51] Int. Cl.$^5$ .................. C07D 403/12; C07D 417/12; C07D 409/12; C07D 405/12
[52] U.S. Cl. ..................................... 544/197; 544/198; 544/206; 544/207; 544/208; 544/209; 544/211; 544/212
[58] Field of Search ............... 544/197, 198, 206, 207, 544/208, 209, 211, 212

[56] References Cited

PUBLICATIONS

Schallner et al., "5-Sulfonamide-1-etc." CA 106:45716m (1987).

*Primary Examiner*—Patricia L. Morris
*Attorney, Agent, or Firm*—Sprung Horn Kramer & Woods

[57] ABSTRACT

Herbicidal substituted sulphonylaminoazoles of the formula

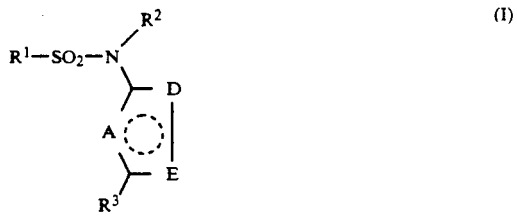

in which
$R^1$ is optionally substituted alkyl, aralkyl, aryl or heteroaryl,
$R^2$ is hydrogen or $-SO_2-R^1$,
$R^3$ is hydrogen, halogen, hydroxyl, mercapto, amino, or an optionally substituted alkyl, alkoxy, alkylthio, alkylamino or dialkylamino radical,
A is CH, nitrogen or,
at least one of A, D and E is

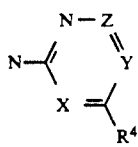

and the others may be that or CH or nitrogen, and
X, Y and Z each is nitrogen or optionally substituted C, and salts thereof.

1 Claim, No Drawings

HERBICIDAL SUBSTITUTED SULPHONYLAMINOAZOLES

This is a division of application Ser. No. 504,442, filed Apr. 3, 1990, now U.S. Pat. No. 5,012,082, which is a division of application Ser. No. 317,219, filed 2/28/89, now U.S. Pat. No. 4,941,912.

The invention relates to novel substituted sulphonylaminoazoles, processes and new intermediates for their preparation and their use as herbicides.

It is known that 3-amino-1,2,4-triazole (amitrole) can be used as a herbicide (cf. Science 145 (1964), 97). However, the action of this compound is not satisfactory in all respects.

The new substituted sulphonylaminoazoles of the general formula (I)

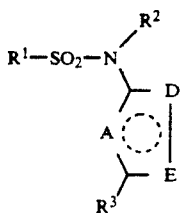
(I)

in which
$R^1$ stands for an optionally substituted radical from the series comprising alkyl, aralkyl, aryl and heteroaryl,
$R^2$ stands for hydrogen or the grouping $-SO_2-R^1$, wherein
$R^1$ has the abovementioned meaning,
$R^3$ stands for hydrogen, halogen, hydroxyl, mercapto, amino or an optionally substituted radical from the series comprising alkyl, alkoxy, alkylthio, alkylamino and dialkylamino,
A stands for a CH grouping, for nitrogen or the grouping

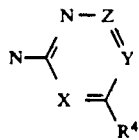

D stands for nitrogen or the grouping

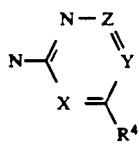

E stands for nitrogen or the grouping

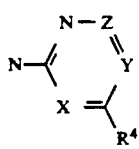

one of each of the radicals A, D or E in each case standing for the grouping

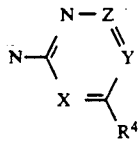

wherein
$R^4$ stands for hydrogen, halogen, hydroxyl, amino or an optionally substituted radical from the series comprising alkyl, alkoxy, alkylthio, alkylamino and dialkylamino,
X stands for nitrogen or a CH grouping,
Y stands for nitrogen or a $CR^5$ grouping wherein
$R^5$ stands for hydrogen, halogen, cyano, alkyl, formyl, alkylcarbonyl or alkoxycarbonyl, and
Z stands for nitrogen or a $CR^6$ grouping wherein
$R^6$ stands for hydrogen, halogen, hydroxyl, amino or an optionally substituted radical from the series comprising alkyl, alkoxy, alkylthio, alkylamino and dialkylamino, and salts of the compounds of the formula (I) have now been found.

The general formula (I) stands for the possible isomers of the formulae (IA), (IB) and (IC)

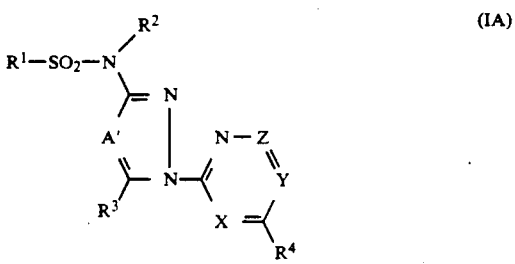
(IA)

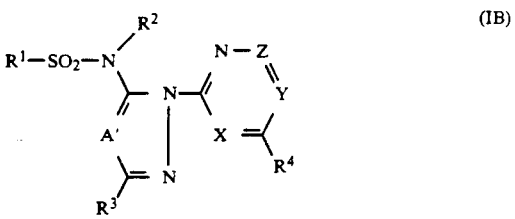
(IB)

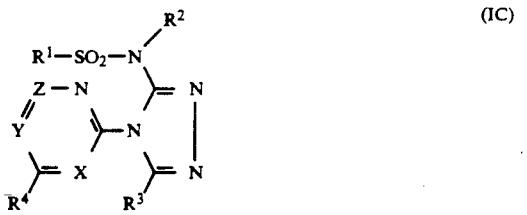
(IC)

in which
$R^1$, $R^2$, $R^3$, $R^4$, X, Y and Z have the abovementioned meanings and
A' stands for nitrogen or a CH grouping,
and for mixtures of these isomers.

The new substituted sulphonylaminoazoles of the general formula (I) are obtained in a process in which
(a) substituted aminoazoles of the general formula (II)

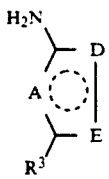 (II)

in which

A, D, E and $R^3$ have the abovementioned meanings, are reacted with sulphonyl halides or sulphonic anhydrides of the general formula (III)

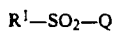 (III)

in which $R^1$ has the abovementioned meaning and

Q stands for fluorine, chlorine, bromine or the grouping $-O-SO_2-R^1$, wherein $R^1$ has the abovementioned meaning, if appropriate in the presence of an acid acceptor, if appropriate in the presence of a catalyst and if appropriate in the presence of a diluent, and in which, if appropriate, the resulting compounds of the formula (I) in which $R^2$ stands for the grouping $-SO_2-R^1$, are reacted with desulphonylating agents, if appropriate in the presence of diluents, to give compounds of the formula (I) in which $R^2$ stands for hydrogen, or in which (b) sulphonylated aminoguanidines of the general formulae (IVA) or (IVB)

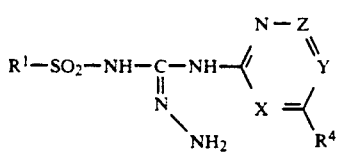 (IVA)

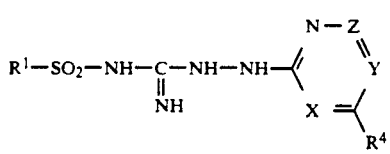 (IVB)

in which $R^1$, $R^4$, X, Y and Z have the abovementioned meanings or tautomers of the compounds of the formulae (IVA) and (IVB) or mixtures of the compounds of the formulae (IVA) or (IVB) and the tautomers possible in each case are reacted with ester(amide)s of the general formula (V) (i.e. orthoesters or amide acetals)

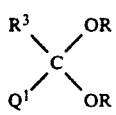 (V)

in which $R^3$ has the abovementioned meaning,

R stands for alkyl and $Q^1$ stands for alkoxy or dialkylamino, if appropriate in the presence of a diluent, or in which (c) substituted aminopyrazolines of the general formula (VI)

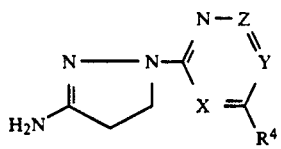 (VI)

in which $R^4$, X, Y and Z have the abovementioned meanings, are reacted with sulphonyl halides or sulphonic anhydrides of the general formula (III)

 (III)

in which $R^1$ has the abovementioned meaning and

Q stands for fluorine, chlorine, bromine or the grouping $-O-SO_2-R^1$ wherein $R^1$ has the abovementioned meaning, in the presence of (atmospheric) oxygen, if appropriate in the presence of an acid acceptor and if appropriate in the presence of a diluent, and if appropriate the resulting compounds of the formula (I), in which $R^2$ stands for the grouping $-SO_2-R^1$, are reacted with desulphonylating agents, if appropriate in the presence of diluents, to give compounds of the formula (I), in which $R^2$ stands for hydrogen, and if appropriate the products obtained by processes (a), (b) or (c) are converted to salts by customary methods.

Some of the compounds of the formula (I) according to the invention can also be obtained as outlined below ($R^1$, $R^4$, X, Y, Z as defined above; $Q^2$ for example $SCH_3$ or $OC_6H_5$):

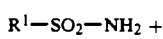 (d)

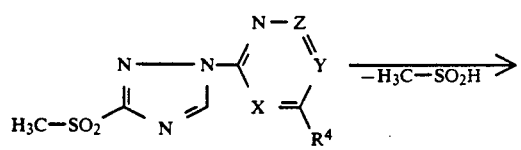

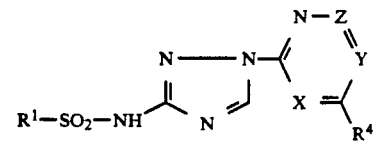

(e)

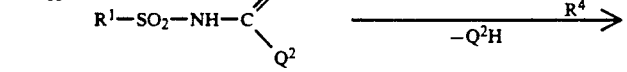

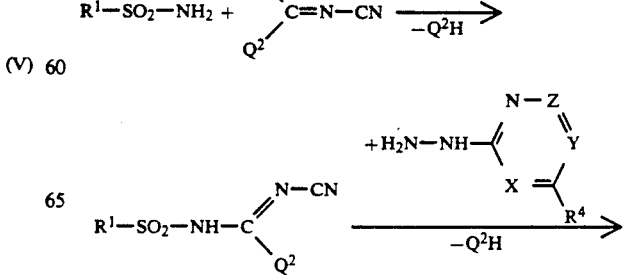

-continued

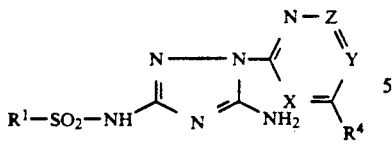

The new substituted sulphonylaminoazoles of the general formula (I) are distinguished by a powerful herbicidal activity. These compounds represent a chemically novel class of herbicides. Surprisingly, the new compounds of the formula (I) show a considerably better herbicidal action than the known herbicide aminotrizole (amitrole) which has a similar structure.

The invention preferably relates to compounds of the formula (I) in which $R^1$ stands for the radical

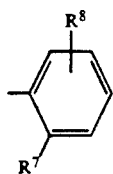

wherein $R^7$ and $R^8$ are identical or different and stand for hydrogen, fluorine, chlorine, bromine, iodine, cyano, nitro, $C_1$–$C_6$-alkyl [which is optionally substituted by fluorine, chlorine, bromine, cyano, carboxyl, $C_1$–$C_4$-alkoxycarbonyl, $C_1$–$C_4$-alkylaminocarbonyl, di-($C_1$–$C_4$-alkyl)-aminocarbonyl, hydroxyl, $C_1$–$C_4$-alkoxy, formyloxy, $C_1$–$C_4$-alkylcarbonyloxy, $C_1$–$C_4$-alkoxycarbonyloxy, $C_1$–$C_4$-alkylamino-carbonyloxy, $C_1$–$C_4$-alkylthio, $C_1$–$C_4$-alkylsulphinyl, $C_1$–$C_4$-alkylsulphonyl, di-($C_1$–$C_4$-alkyl)-aminosulphonyl, $C_3$–$C_6$-cycloalkyl or phenyl], for $C_2$–$C_6$-alkenyl [which is optionally substituted by fluorine, chlorine, bromine, cyano, $C_1$–$C_4$-alkoxy-carbonyl, carboxyl or phenyl], for $C_2$–$C_6$-alkinyl [which is optionally substituted by fluorine, chlorine, bromine, cyano, $C_1$–$C_4$-alkoxycarbonyl, carboxyl or phenyl], for $C_1$–$C_4$-alkoxy [which is optionally substituted by fluorine, chlorine, bromine, cyano, carboxyl, $C_1$–$C_4$-alkoxycarbonyl, $C_1$–$C_4$-alkoxy, $C_1$–$C_4$-alkylthio, $C_1$–$C_4$-alkylsulphinyl or $C_1$–$C_4$-alkylsulphonyl], for $C_1$–$C_4$-alkylthio [which is optionally substituted by fluorine, chlorine, bromine, cyano, carboxyl, $C_1$–$C_4$-alkoxy-carbonyl, $C_1$–$C_4$-alkylthio, $C_1$–$C_4$-alkylsulphinyl or $C_1$–$C_4$-alkylsulphonyl], for $C_3$–$C_6$-alkenyloxy [which is optionally substituted by fluorine, chlorine, bromine, cyano or $C_1$–$C_4$-cyano or $C_1$–$C_4$-alkoxycarbonyl], for $C_2$–$C_6$-alkenylthio [which is optionally substituted by fluorine, chlorine, bromine, cyano, nitro, $C_1$–$C_3$-alkylthio or $C_1$–$C_4$-alkoxycarbonyl], $C_3$–$C_6$-alkinyloxy, $C_3$–$C_6$-alkinylthio or for the radical —S(O)$_p$—$R^9$, p standing for the numbers 1 or 2 and $R^9$ standing for $C_1$–$C_4$-alkyl [which is optionally substituted by fluorine, chlorine, bromine, cyano or $C_1$–$C_4$-alkoxy-carbonyl], $C_3$–$C_6$-alkenyl, $C_3$–$C_6$-alkinyl, $C_1$–$C_4$-alkoxy, $C_1$–$C_4$-alkoxy-$C_1$–$C_4$-alkylamino, $C_1$–$C_4$-alkylamino, di-($C_1$–$C_4$-alkyl)-amino or for the radical —NHOR$^{10}$, $R^{10}$ standing for $C_1$–$C_6$-alkyl [which is optionally substituted by fluorine, chlorine, cyano, $C_1$–$C_4$-alkoxy, $C_1$–$C_4$-alkylthio, $C_1$–$C_4$-alkylsulphinyl, $C_1$–$C_4$-alkylsulphonyl, $C_1$–$C_4$-alkyl-carbonyl, $C_1$–$C_4$-alkoxy-carbonyl, $C_1$–$C_4$-alkylamino-carbonyl or di-($C_1$–$C_4$-alkyl)-amino-carbonyl], for $C_3$–$C_6$-alkenyl [which is optionally substituted by fluorine, chlorine or bromine], $C_3$–$C_6$-alkinyl, $C_3$–$C_6$-cycloalkyl, $C_3$–$C_6$-cycloalkyl-$C_1$–$C_2$-alkyl, phenyl-$C_1$–$C_2$-alkyl [which is optionally substituted by fluorine, chlorine, nitro, cyano, $C_1$–$C_4$-alkyl, $C_1$–$C_4$-alkoxy or $C_1$–$C_4$-alkoxy-carbonyl], for benzhydryl or for phenyl [which is optionally substituted by fluorine, chlorine, nitro, cyano, $C_1$–$C_4$-alkyl, trifluoromethyl, $C_1$–$C_4$-alkoxy, $C_1$–$C_2$-fluoroalkoxy, $C_1$–$C_4$-alkylthio, trifluoromethylthio or $C_1$–$C_4$-alkoxy-carbonyl], $R^7$ and $R^8$ furthermore stand for phenyl or phenoxy, for $C_1$–$C_4$-alkylcarbonylamino, $C_1$–$C_4$-alkoxycarbonylamino, $C_1$–$C_4$-alkylamino-carbonylamino, di-($C_1$–$C_4$-alkyl)-amino-carbonylamino, or for the radical —CO—$R^{11}$, $R^{11}$ standing for $C_1$–$C_6$-alkyl, $C_1$–$C_6$-alkoxy, $C_3$–$C_6$-cycloalkoxy, $C_3$–$C_6$-alkenyloxy, $C_1$–$C_4$-alkylthio, amino, $C_1$–$C_4$-alkylamino, $C_1$–$C_4$-alkoxyamino, $C_1$–$C_4$-alkoxy-$C_1$–$C_4$-alkyl-amino or di-($C_1$–$C_4$-alkyl)-amino [which are optionally substituted by fluorine and/or chlorine], $R^7$ and $R^8$ furthermore stand for $C_1$–$C_4$-alkylsulphonyloxy, di-($C_1$–$C_4$-alkyl)-aminosulphonylámino or for the radical —CH=N—$R^{12}$, $R^{12}$ standing for $C_1$–$C_6$-alkyl which is optionally substituted by fluorine, chlorine, cyano, carboxyl, $C_1$–$C_4$-alkoxy, $C_1$–$C_4$-alkylthio, $C_1$–$C_4$-alkylsulphinyl or $C_1$–$C_4$-alkylsulphonyl, for benzyl which is optionally substituted by fluorine or chlorine, for $C_3$–$C_6$-alkenyl or $C_3$–$C_6$-alkinyl, each of which is optionally substituted by fluorine or chlorine, for phenyl which is optionally substituted by fluorine, chlorine, bromine, $C_1$–$C_4$-alkyl, $C_1$–$C_4$-alkoxy, trifluoromethyl, trifluoromethoxy or trifluoromethylthio, for $C_1$–$C_6$-alkoxy, $C_3$–$C_6$-alkenoxy, $C_3$–$C_6$-alkinoxy or benzyloxy, each of which is optionally substituted by fluorine and/or chlorine, for amino, $C_1$–$C_4$-alkylamino, di-($C_1$–$C_4$-alkyl)-amino, phenylamino, $C_1$–$C_4$-alkyl-carbonylamino, $C_1$–$C_4$-alkoxy-carbonylamino, $C_1$–$C_4$-alkylsulphonylamino or for phenylsulphonylamino which is optionally substituted by fluorine, chlorine, bromine or methyl, wherein furthermore $R^1$ stands for the radical

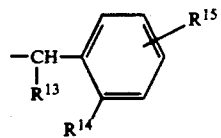

wherein $R^{13}$ stands for hydrogen or $C_1$–$C_4$-alkyl, $R^{14}$ and $R^{15}$ are identical or different and stand for hydrogen, fluorine, chlorine, bromine, nitro, cyano, $C_1$–$C_4$-alkyl [which is optionally substituted by fluorine and/or chlorine], $C_1$–$C_4$-alkoxy [which is optionally substituted by fluorine and/or chlorine], carboxyl, $C_1$–$C_4$-alkoxy-carbonyl, $C_1$–$C_4$-alkylsulphonyl or di-($C_1$–$C_4$-alkyl)aminosulphonyl;

wherein furthermore

R¹ stands for the radical

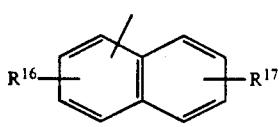

wherein

R¹⁶ and R¹⁷ are identical or different and stand for hydrogen, fluorine, chlorine, bromine, nitro, cyano, C₁-C₄-alkyl [which is optionally substituted by fluorine and/or chlorine] or C₁-C₄-alkoxy [which is optionally substituted by fluorine and/or chlorine];

wherein furthermore

R¹ stands for the radical

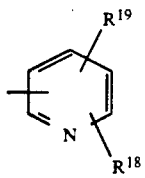

wherein

R¹⁸ and R¹⁹ are identical or different and stand for hydrogen, fluorine, chlorine, bromine, nitro, cyano, C₁-C₄-alkyl [which is optionally substituted by fluorine and/or chlorine], C₂-C₄-alkenyl [which is optionally substituted by fluorine and/or chlorine], C₁-C₄-alkoxy [which is optionally substituted by fluorine and/or chlorine], for C₁-C₄-alkylthio, C₁-C₄-alkylsulphinyl or C₁-C₄-alkylsulphonyl [which are optionally substituted by fluorine and/or chlorine], and for di-(C₁-C₄-alkyl)aminosulphonyl, C₁-C₄-alkoxy-carbonyl, dimethylaminocarbonyl or dioxolanyl;

wherein furthermore

R¹ stands for the radical

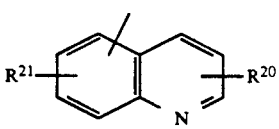

wherein

R²⁰ and R²¹ are identical or different and stand for hydrogen, fluorine, chlorine, bromine, C₁-C₄-alkyl [which is optionally substituted by fluorine and/or bromine], C₁-C₄-alkoxy [which is optionally substituted by fluorine and/or chlorine], for C₁-C₄-alkylthio, C₁-C₄-alkylsulphinyl or C₁-C₄-alkylsulphonyl [which are optionally substituted by fluorine and/or chlorine], or for di-(C₁-C₄-alkyl)-aminosulphonyl;

wherein furthermore

R¹ stands for the radical

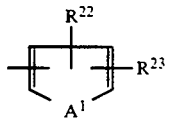

wherein

R²² and R²³ are identical or different and stand for hydrogen, fluorine, chlorine, bromine, cyano, nitro, C₁-C₄-alkyl [which is optionally substituted by fluorine, chlorine, C₁-C₄-alkoxy and/or C₁-C₄-halogenoalkoxy], C₁-C₄-alkoxy [which is optionally substituted by fluorine and/or chlorine], C₁-C₄-alkylthio, C₁-C₄-alkylsulphinyl or C₁-C₄-alkylsulphonyl [which is optionally substituted by fluorine and/or chlorine], di-(C₁-C₄-alkyl)-aminosulphonyl or C₁-C₄-alkoxycarbonyl, and A¹ stands for oxygen, sulphur or the grouping N—Z¹, Z¹ standing for hydrogen, C₁-C₄-alkyl [which is optionally substituted by fluorine, chlorine, bromine or cyano], C₃-C₆-cycloalkyl, benzyl, phenyl [which is optionally substituted by fluorine, chlorine, bromine or nitro], C₁-C₄-alkylcarbonyl, C₁-C₄-alkoxy-carbonyl or di-(C₁-C₄-alkyl)-aminocarbonyl;

wherein furthermore

R¹ stands for the radical

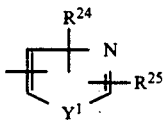

wherein

R²⁴ and R²⁵ are identical or different and stand for hydrogen, C₁-C₄-alkyl, halogen, C₁-C₄-alkoxycarbonyl, C₁-C₄-alkoxy or C₁-C₄-halogenoalkoxy, Y¹ stands for sulphur or the grouping N—R²⁶, R²⁶ standing for hydrogen or C₁-C₄-alkyl;

wherein furthermore

R¹ stands for the radical

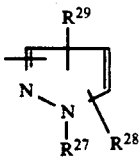

wherein

R²⁷ stands for hydrogen, C₁-C₄-alkyl, phenyl or (iso)-quinolinyl,

R²⁸ stands for hydrogen, halogen, cyano, nitro, C₁-C₄-alkyl [which is optionally substituted by fluorine and/or chlorine], C₁-C₄-alkoxy [which is optionally substituted by fluorine and/or chlorine], dioxolanyl or C₁-C₄-alkoxy-carbonyl and R²⁹ stands for hydrogen, halogen or C₁-C₄-alkyl;

wherein furthermore

R¹ stands for the radical

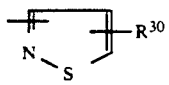

wherein
R$^{30}$ stands for hydrogen, halogen, C$_1$-C$_4$-alkyl or C$_1$-C$_4$-alkoxy-carbonyl;
wherein furthermore
R$^1$ stands for the radical

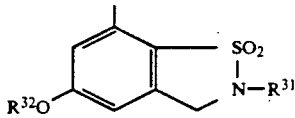

wherein
R$^{31}$ stands for C$_1$-C$_4$-alkyl and
R$^{32}$ stands for C$_1$-C$_4$-alkyl,
wherein furthermore
R$_1$ stands for the radical

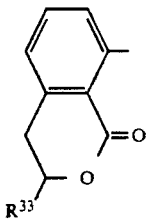

wherein
R$^{33}$ stands for hydrogen or methyl;
in which furthermore
R$^2$ stands for hydrogen or for the grouping —SO$_2$—R$^1$,
wherein
R$^1$ has the preferred meaning given above;
in which furthermore
R$^3$ stands for hydrogen, fluorine, chlorine, bromine, iodine, hydroxyl, mercapto, amino or for a radical from the series comprising C$_1$-C$_4$-alkyl, C$_1$-C$_4$-alkoxy, C$_1$-C$_4$-alkylthio, C$_1$-C$_4$-alkylamino and di-(C$_1$-C$_4$-alkyl)amino, which radical is optionally substituted by fluorine and/or chlorine,
A stands for nitrogen, a CH grouping or the grouping

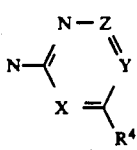

D stands for nitrogen or the grouping

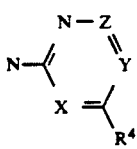

E stands for nitrogen or the grouping

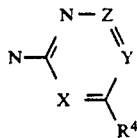

one of each of the radicals A, D or E in each case standing for the grouping

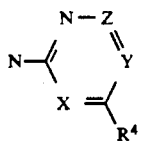

wherein
R$^4$ stands for hydrogen, fluorine, chlorine, bromine, C$_1$-C$_4$-alkyl, C$_1$-C$_4$-halogenoalkyl, C$_1$-C$_2$-alkoxy-C$_1$-C$_2$-alkyl, C$_1$-C$_4$-alkoxy, C$_1$-C$_4$-halogenoalkoxy, C$_1$-C$_4$-alkylthio, C$_1$-C$_4$-halogenoalkylthio, amino, C$_1$-C$_4$-alkyl-amino, dimethylamino or diethylamino,
X stands for nitrogen or a CH grouping,
Y stands for nitrogen or a CR$^5$ grouping,
wherein
R$^5$ stands for hydrogen, fluorine, chlorine, bromine, cyano, methyl, formyl, acetyl, methoxycarbonyl or ethoxycarbonyl and
Z stands for nitrogen or a CR$^6$ grouping
wherein
R$^6$ stands for hydrogen, fluorine, chlorine, bromine, C$_1$-C$_4$-alkyl, C$_1$-C$_4$-halogenoalkyl, C$_1$-C$_4$-alkoxy, C$_1$-C$_4$-halogenoalkoxy, C$_1$-C$_4$-alkylthio, C$_1$-C$_4$-alkyl-amino, dimethylamino or diethylamino.

In particular, the invention relates to compounds of the formula (I) in which
R$^1$ stands for the radial

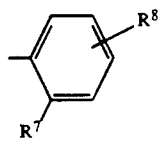

wherein
R$^7$ stands for flourine, chlorine, bromine, methyl, trifluoromethyl, methoxy, difluoromethoxy, trifluoromethoxy, C$_1$-C$_3$-alkylthio, C$_1$-C$_3$-alkylsulphinyl, C$_1$-C$_3$-alkylsulphonyl, dimethylaminosulphonyl, N-methoxy-N-methylaminosulphonyl, phenyl, phenoxy or C$_1$-C$_3$-alkoxy-carbonyl and
R$^8$ stands for hydrogen, fluorine or chlorine;
wherein furthermore
R$^1$ stands for the radical

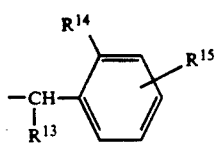

wherein
R$^{13}$ stands for hydrogen, $R^{14}$ stands for fluorine, chlorine, bromine, methyl, methoxy, difluoromethoxy, trifluoromethoxy, ethoxy, methoxycarbonyl, ethoxycarbonyl, methylsulphonyl or dimethylaminosulphonyl and $R^{15}$ stands for hydrogen, fluorine or chlorine;
wherein furthermore
$R^1$ stands for the radical

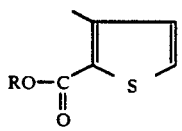

wherein
R stands for $C_1$-$C_4$-alkyl, or
$R^1$ stands for the radical

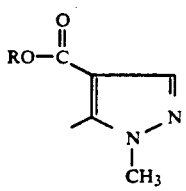

wherein
R stands for $C_1$-$C_4$-alkyl, or
$R^1$ stands for the radical

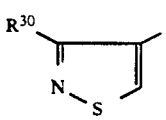

wherein
$R^{30}$ stands for hydrogen, chlorine, methyl, ethyl, methoxycarbonyl or ethoxycarbonyl; in which furthermore
$R^2$ stands for hydrogen or for the grouping —$SO_2$—$R^1$,
wherein
$R^1$ has the meaning given above as particularly preferred,
$R^3$ stands for hydrogen, methyl, methoxy or methylthio,
A stands for nitrogen, a CH grouping or the grouping

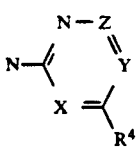

D stands for nitrogen or the grouping

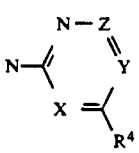

E stands for nitrogen or the grouping

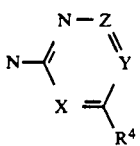

one of each of the radicals A, D or E in each case standing for the grouping

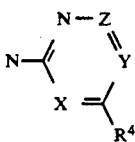

wherein
$R^4$ stands for hydrogen, fluorine, chlorine, bromine, methyl, trifluoromethyl, methoxy, ethoxy, difluoromethoxy, methylthio, ethylthio, amino, methylamino, ethylamino, dimethylamino or diethylamino, X stands for nitrogen or a CH grouping, Y stands for nitrogen or a $CR^5$ grouping,
wherein
$R^5$ stands for hydrogen, fluorine, chlorine or methyl, and Z stands for nitrogen or a $CR^6$ grouping
wherein
$R^6$ stands for hydrogen, fluorine, chlorine, bromine, methyl, ethyl, trifluoromethyl, methoxy, ethoxy, propoxy, isopropoxy, difluoromethoxy, methylthio, ethylthio, methylamino, ethylamino, dimethylamino or diethylamino.

Very particularly preferred compounds of the formula (IA)—above—are those in which $R^1$, $R^2$, $R^3$, $R^4$, X, Y and Z have those meanings which have been mentioned in connection with the description of the compounds of the formula (I) according to the invention as being particularly preferred for $R^1$, $R^2$, $R^3$, $R^4$, X, Y and Z. A' particularly preferably stands for nitrogen or a CH grouping.

Furthermore particularly preferred compounds of the general formula (IB)—above—in which $R^1$, $R^2$, $R^3$, $R^4$, X, Y and Z have those meanings which have been mentioned in connection with the description of the compounds of the formula (I) according to the invention as being particularly preferred for $R^1$, $R^2$, $R^3$, $R^4$, X, Y and Z. A' particularly preferably stands for nitrogen or a CH grouping.

Moreover, particularly preferred compounds of the general formula (IC)—above—are those in which $R^1$, $R^2$, $R^3$, $R^4$, X, Y and Z have those meanings which have been mentioned in connection with the description of the compounds of the formula (I) according to the invention as being particularly preferred for $R^1$, $R^2$, $R^3$, $R^4$, X, Y and Z.

The invention furthermore relates to salts of compounds of the formula (I) formed with α) protonic acids, such as, for example, hydrochloric acid, sulphuric acid, phosphoric acid, methanesulphonic acid, benzene- or p-toluenesulphonic acid, or naphthalenemono- or di-sulphonic acids, or β) bases, such as, for example, the hydroxides, hydrides, amides or carbonates of sodium, potassium or calcium, sodium $C_1$-$C_4$-alkanoxides, potassium $C_1$-$C_4$- alkanoxides, ammonia, $C_1$-$C_4$-alkylamines, di-($C_1$-$C_4$-alkyl)-amines or tri-($C_1$-$C_4$-alkyl)-amines.

If, for example, 5-amino-3-methyl-1-(4,6-dimethoxy-1,3,5-triazin-2-yl)-1,2,4-triazole and 2-fluorobenzenesulphonyl chloride (2 mole equivalents) are used as starting substances, the course of the reaction in the process (a) according to the invention can be outlined by the following equation:

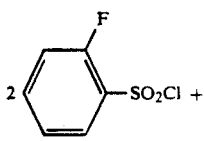

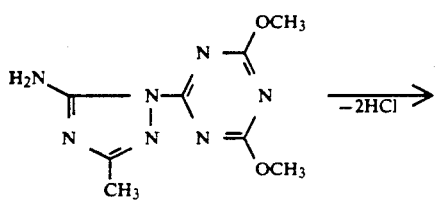

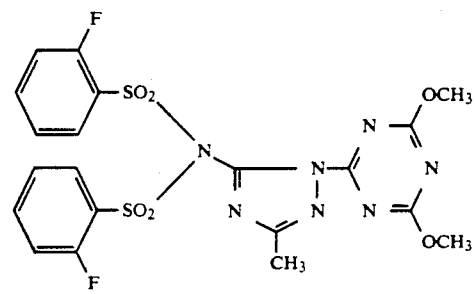

If, for example, N'-(4,6-dimethoxy-pyrimidin-2-yl-amino)-N''-(2-methoxycarbonyl-benzylsulphonyl)-guanidine and trimethyl orthoformate are used as starting substances, the course of the reaction in process (b) according to the invention can be outlined by the following equation:

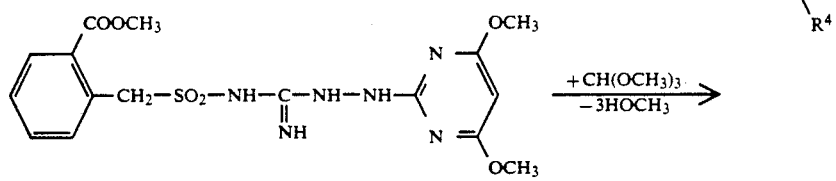

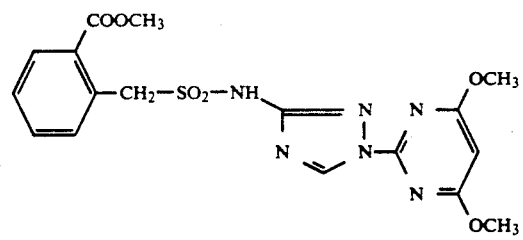

If, for example, 3-amino-1-(4,6-dimethylpyrimidin-2-yl)-2-pyrazoline and 2-methylsulphonylbenzenesulphonyl chloride are used as starting substances, and if the reaction is carried out under an (atmospheric) oxygen atmosphere, the course of the reaction in process (c) according to the invention can be outlined by the following equation:

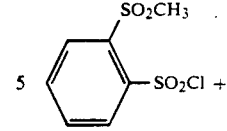

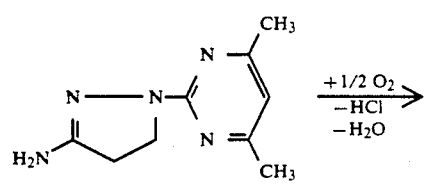

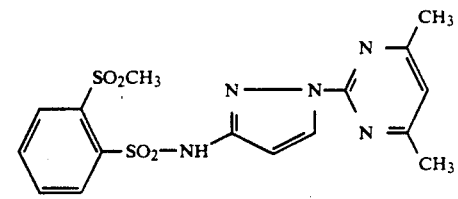

Formula (II) provides a general definition of the substituted aminoazoles to be used as starting substances in process (a) according to the invention for the preparation of compounds of the formula (I).

In formula (II), A, D, E and $R^3$ preferably, or in particular, have those meanings which have already been preferentially mentioned above, or mentioned above as particularly preferred, for A, D, E and $R^3$ in connection with the description of the compounds of the formula (I) according to the invention.

The general formula (II) stands for the possible isomers of the formulae (IIA), (IIB) and (IIC)

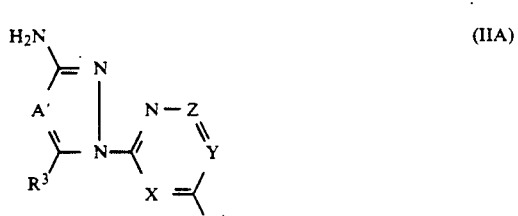

(IIA)

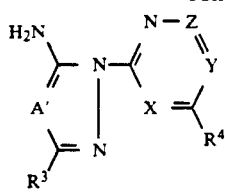

(IIB)

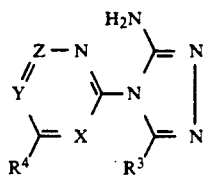

(IIC)

and for mixtures of these isomers.

In formulae (IIA), (IIB) and (IIC), A', $R^3$, $R^4$, X, Y and Z preferably, or in particular, have those meanings which have already been preferentially mentioned above, or mentioned as particularly preferred, for A', $R^3$, $R^4$, X, Y and Z in connection with the description of the compounds of the formula (I) according to the invention.

Examples of the starting substances of the formulae (IIA), (IIB) and (IIC)—and thus also for the compounds of the formula (II)—are listed in Table 1 below. Thus, the meanings of the variables A, $R^3$, $R^4$, X, Y and Z, each of which is indicated line by line for individual examples, in each individual case stand for the isomers of the formulae (IIA), (IIB) and for the isomers of the formula (IIC).

TABLE 1

Examples of the starting substances of the formulae (IIA), (IIB) and (IIC)

| A or A' | $R^3$ | $R^4$ | X | Y | Z |
|---|---|---|---|---|---|
| N | H | $CH_3$ | N | CH | $C-CH_3$ |
| N | H | $CH_3$ | N | CH | $C-OCH_3$ |
| N | H | $CH_3$ | N | CH | $C-OC_2H_5$ |
| N | H | $OCH_3$ | N | CH | $C-OCH_3$ |
| N | H | $OCH_3$ | N | CH | $C-Cl$ |
| N | H | H | N | CH | $C-CH_3$ |

TABLE 1-continued

Examples of the starting substances of the formulae (IIA), (IIB) and (IIC)

| | | | | | |
|---|---|---|---|---|---|
| N | H | $CF_3$ | N | CH | $C-OCH_3$ |
| N | H | $OCH_3$ | N | CH | $C-OCHF_2$ |
| N | H | $CH_3$ | N | CH | $C-OCHF_2$ |
| N | H | $OCHF_2$ | N | CH | $C-OCHF_2$ |
| N | H | $CH_3$ | N | N | $C-CH_3$ |
| N | H | $CH_3$ | N | N | $C-OCH_3$ |
| N | H | $OCH_3$ | N | N | $C-OCH_3$ |
| N | H | $OCH_3$ | N | N | $C-Cl$ |
| N | H | $C_2H_5$ | N | CH | $C-OCH_3$ |
| N | H | $C_2H_5$ | N | N | $C-OCH_3$ |
| N | $CH_3$ | $CH_3$ | N | CH | $C-CH_3$ |
| N | $CH_3$ | $CH_3$ | N | CH | $C-OCH_3$ |
| N | $CH_3$ | $OCH_3$ | N | CH | $C-OCH_3$ |
| N | $CH_3$ | $OCH_3$ | N | CH | $C-Cl$ |
| N | $CH_3$ | H | N | CH | $C-CH_3$ |
| N | $CH_3$ | $CF_3$ | N | CH | $C-OCH_3$ |
| N | $CH_3$ | $OCH_3$ | N | CH | $C-OCHF_2$ |
| N | $CH_3$ | $CH_3$ | N | CH | $C-OCHF_2$ |
| N | $CH_3$ | $CH_3$ | N | N | $C-CH_3$ |
| N | $CH_3$ | $CH_3$ | N | N | $C-OCH_3$ |
| N | $CH_3$ | $OCH_3$ | N | N | $C-OCH_3$ |
| N | $CH_3$ | $C_2H_5$ | N | CH | $C-OCH_3$ |
| N | $CH_3$ | $CH_3$ | N | N | $C-OC_2H_5$ |
| N | $CH_3$ | $C_2H_5$ | N | N | $C-OCH_3$ |
| N | $CH_3$ | $CH_3$ | N | N | $C-Cl$ |
| N | $CH_3$ | $CH_3$ | CH | N | $C-CH_3$ |
| N | $CH_3$ | $OCH_3$ | CH | N | $C-OCH_3$ |
| N | $CH_3$ | $CH_3$ | N | CH | $C-SCH_3$ |
| N | H | $CH_3$ | N | CH | $C-N(CH_3)_2$ |
| N | H | $OCH_3$ | N | CH | $C-SCH_3$ |
| N | H | $OCH_3$ | N | N | $C-NHC_2H_5$ |
| N | H | $OC_2H_5$ | N | N | $C-NHCH_3$ |
| N | H | $CH_3$ | CH | CH | $C-CH_3$ |
| N | $OCH_3$ | $CH_3$ | N | CH | $C-CH_3$ |
| N | $OCH_3$ | $CH_3$ | N | CH | $C-OCH_3$ |
| N | $OCH_3$ | $OCH_3$ | N | CH | $C-OCH_3$ |
| N | $OCH_3$ | $OCH_3$ | N | CH | $C-Cl$ |
| N | $OCH_3$ | H | N | CH | $C-CH_3$ |
| N | $OCH_3$ | $CF_3$ | N | CH | $C-OCH_3$ |
| N | $OCHF_2$ | $OCH_3$ | N | CH | $C-OCHF_2$ |
| N | $OCH_3$ | $CH_3$ | N | CH | $C-OCHF_2$ |
| N | $OCH_3$ | $CH_3$ | N | N | $C-CH_3$ |
| N | $OCH_3$ | $CH_3$ | N | N | $C-OCH_3$ |
| N | $OCH_3$ | $OCH_3$ | N | N | $C-OCH_3$ |
| N | $OCH_3$ | $C_2H_5$ | N | CH | $C-OCH_3$ |
| N | $OCH_3$ | $C_2H_5$ | N | N | $C-OCH_3$ |
| N | $SCH_3$ | $CH_3$ | N | CH | $C-CH_3$ |
| N | $OCH_3$ | $CH_3$ | N | N | $C-OC_2H_5$ |
| N | $SCH_3$ | $CH_3$ | N | CH | $C-OCH_3$ |
| N | $SCH_3$ | $CH_3$ | N | CH | $C-OC_2H_5$ |
| N | $SCH_3$ | $OCH_3$ | N | CH | $C-OCH_3$ |
| N | $SCH_3$ | $OCH_3$ | N | CH | $C-Cl$ |
| N | $SCH_3$ | H | N | CH | $C-CH_3$ |
| N | $SCH_3$ | $CF_3$ | N | CH | $C-OCH_3$ |
| N | $SCH_3$ | $OCH_3$ | N | CH | $C-OCHF_2$ |
| N | $SCH_3$ | $CH_3$ | N | CH | $C-OCHF_2$ |
| N | $SCH_3$ | $OCHF_2$ | N | CH | $C-OCHF_2$ |
| N | $SCH_3$ | $CH_3$ | N | N | $C-CH_3$ |
| N | $SCH_3$ | $CH_3$ | N | N | $C-OCH_3$ |
| N | $SCH_3$ | $OCH_3$ | N | N | $C-OCH_3$ |
| N | $SCH_3$ | $OCH_3$ | N | N | $C-Cl$ |
| N | $SCH_3$ | $C_2H_5$ | N | CH | $C-OCH_3$ |
| N | $SCH_3$ | $C_2H_5$ | N | N | $C-OCH_3$ |
| CH | H | $CH_3$ | N | CH | $C-CH_3$ |
| CH | H | $CH_3$ | N | CH | $C-OCH_3$ |
| CH | H | $OCH_3$ | N | CH | $C-OCH_3$ |
| CH | H | $OCH_3$ | N | CH | $C-Cl$ |
| CH | H | $CF_3$ | N | CH | $C-OCH_3$ |
| CH | H | $OCH_3$ | N | CH | $C-OCHF_2$ |
| CH | H | $CH_3$ | N | CH | $C-OCHF_2$ |
| CH | H | $OCHF_2$ | N | CH | $C-OCHF_2$ |
| CH | H | $CH_3$ | N | N | $C-CH_3$ |
| CH | H | $CH_3$ | N | N | $C-OCH_3$ |
| CH | H | $OCH_3$ | N | N | $C-Cl$ |
| CH | H | $C_2H_5$ | N | CH | $C-OCH_3$ |
| CH | H | $C_2H_5$ | N | N | $C-OCH_3$ |

Most of the starting substances of the formula (II)- —and also those of the formulae (IIA), (IIB) and (IIC- )—were hitherto not known from the literature. New compounds of the formula (II) and of the formulae (IIA), (IIB) and (IIC) are, in particular, those in which A, or A', stands for nitrogen.

The compounds of the formula (II) are generally obtained as variously composed mixtures of compounds of the formulae (IIA), (IIB) and (IIC) in a process in which α) aminoazoles of the general formula (VII)

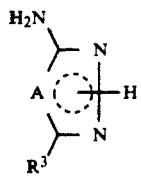
(VII)

in which
A' and $R^3$ have the abovementioned meanings,
are reacted with azines of the general formula (VIII)

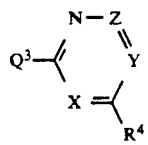
(VIII)

in which
$R^4$, X, Y and Z have the abovementioned meanings and
$Q^3$ stands for halogen or alkylsulphonyl,
if appropriate in the presence of an acid acceptor, such as, for example, potassium carbonate, and if appropriate in the presence of a diluent, such as, for example, acetonitrile or dimethylformamide, at temperatures from 0° C. to 150° C. or in which β) hydrazinoazines of the general formula (IX)

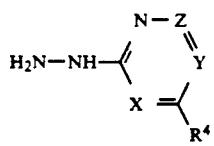
(IX)

in which
$R^4$, X, Y and Z have the abovementioned meanings,
are reacted with S,S-dimethyl cyaniminodithiocarbonate of the formula (X)

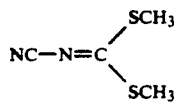
(X)

if appropriate in the presence of a diluent, such as, for example, methanol or ethanol, at temperatures from 0° C. to 100° C., or in which γ) aminoguanidines of the general formula (XIA) or (XIB)

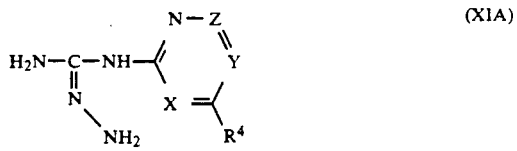
(XIA)

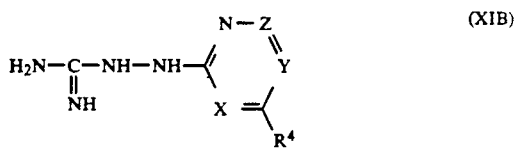
(XIB)

in which
$R^4$, X, Y and Z have the abovementioned meanings, or acid salts thereof, such as, for example, the hydrochlorides,
are reacted with ester(amide)s of the general formula (V)

(V)

in which
$R^3$, R and $Q^1$ have the abovementioned meanings,
if appropriate in the presence of a diluent, such as, for example, acetonitrile or dimethylformamide, at temperatures from 0° C. to 150° C.

Formula (VII) provides a general definition of the aminoazoles required as intermediates for this reaction. In formula (VII), A' and $R^3$ preferably, or in particular, have those meanings which have already been preferentially mentioned above, or mentioned as particularly preferred, for A' and $R^3$ in connection with the description of the compounds of the formula (I) according to the invention.

Examples of the compounds of the formula (VII) which may be mentioned are: 3-amino-1,2,4-triazole, 3-amino-5-methyl-1,2,4-triazole, 3-amino-5-methoxy-1,2,4-triazole, 3-amino-5-methylthio-1,2,4-triazole, 3-aminopyrazole, 3-amino-5-methyl-pyrazole, 3-amino-5-methoxypyrazole and 3-amino-5-methylthio-pyrazole.

The aminoazoles of the formula (VII) are known and/or can be prepared by processes known per se (cf. J. Org. Chem. 28 (1963), 1816–1821; loc. cit. 39 (1974), 1522–1526).

Formula (VIII) provides a general definition of the azines also required as intermediates. In formula (VIII), $R^4$, X, Y and Z preferably, or in particular, have those meanings which have already been preferentially mentioned above, or mentioned above as particularly preferred, for $R^4$, X, Y and Z in connection with the description of the compounds of the formula (I) according to the invention, and $Q^1$ preferably stands for fluorine, chlorine, bromine or $C_1$-$C_4$-alkylsulphonyl, in particular for chlorine or methylsulphonyl.

Examples of the compounds of the formula (VIII) which may be mentioned are: 2-chloro- and 2-methylsulphonyl-4,6-dimethyl-pyrimidine, -4-methyl-6-methoxy-pyrimidine, -4,6-dimethoxy-pyrimidine, -4-methyl-6-ethoxy-pyrimidine, -4-chloro-6-methoxy-pyrimidine, -4-methyl-pyrimidine, -4-chloro-6-methyl-pyrimidine, -4-trifluoromethyl-6-methoxy-pyrimidine, -4-methoxy-6-difluoromethoxy-pyrimidine, -4-methyl- 6-difluoromethoxy-pyrimidine, -4,6-bis-difluoromethoxy-pyrimidine, -4-chloro-6-ethoxy-pyrimidine, -4,6-diethoxy-pyrimidine, -4,5-dichloro-6-methyl-pyrimidine, -4-methyl-5-chloro-6-methoxy-pyrimidine, -4,6-dichloro-pyrimidine, -4-ethyl-6-methoxy-pyrimidine, -5-chloro-4,6-dimethoxy-pyrimidine and -4,6-bis-trifluoromethyl-pyrimidine, furthermore 2-chloro-4,6-dimethyl-s-triazine 2-chloro-4-methyl-6-methoxy-s-triazine, 2-chloro-4,6-dimethoxy-s-triazine, 2,4-dichloro-6-methoxy-s-triazine, 2-chloro-4-ethyl-6-methoxy-s-triazine and 2-chloro-4-methyl-6-ethoxy-s-triazine.

The azines of the formula (VIII) are known and/or can be prepared by processes known per se (cf. J. Chem. Soc. 1957, 1830, 1833; J. Org. Chem. 26 (1961), 792; U.S. Pat. No. 3,308,119 and U.S. Pat. No. 4,711,959).

Formula (IX) provides a general definition of the hydrazinoazines also required as intermediates. In formula (IX), $R^4$, X, Y and Z preferably, or in particular, have those meanings which have already been preferentially mentioned above, or mentioned above as particularly preferred, for $R^4$, X, Y and Z in connection with the description of the compounds of the formula (I) according to the invention.

Examples of the compounds of the formula (IX) which may be mentioned are: 2-hydrazino-4,6-dimethyl-pyrimidine, 4-methyl-6-methoxypyrimidine, -4,6-dimethoxy-pyrimidine, -4-methyl-6-ethoxypyrimidine, -4-chloro-6-methoxy-pyrimidine, -4-methylpyrimidine, -4-chloro-6-methyl-pyrimidine, -4-trifluoromethyl-6-methoxy-pyrimidine, -4-methoxy-6-difluoromethoxypyrimidine, -4-methyl-6-difluoromethoxy-pyrimidine, -4,6-bis-difluoromethoxy-pyrimidine, -4-chloro-6-ethoxypyrimidine, -4,6-diethoxy-pyrimidine, -4,5-dichloro-6-methyl-pyrimidine, -4-methyl-5-chloro-6-methoxy-pyrimidine, -4,6-dichloro-pyrimidine, -4-ethyl-6-methoxy-pyrimidine, -5-chloro-4,6-dimethoxy-pyrimidine and also -4,6-bis-trifluoromethyl-pyrimidine, furthermore 2-hydrazino-4,6-dimethyl-s-triazine, -4-methyl-6-methoxy-s-triazine, -4,6-dimethoxy-s-triazine, -4-ethyl-6-methoxy-s-triazine and -4-methyl-6-ethoxy-s-triazine.

The hydrazinoazines of the formula (IX) are known and/or can be prepared by processes known per se (cf. Chem. Pharm. Bull. 11 (1963), 1382–1388).

In general, the compounds of the formula (IX) are obtained when azines of the formula (VIII)—above—are reacted with hydrazine or hydrazine hydrate, if appropriate in the presence of a diluent, such as, for example, ethanol, acetone, acetonitrile or dimethylformamide, and if appropriate in the presence of a base, such as, for example, potassium carbonate or triethylamine, at temperatures from 0° C. to 100° C.

S,S-Dimethyl cyaniminodithiocarbonate, of the formula (X), which is also required as an intermediate, is already known (cf. J. Org. Chem. 32 (1967), 1566–1572).

Formulae (XIA) and (XIB) provide general definitions of the aminoguanidines also required as intermediates. In formulae (XIA) and (XIB), $R^4$, X, Y and Z preferably, or in particular, have the meanings which have already been preferentially mentioned above, or mentioned above as particularly preferred, for $R^4$, X, Y and Z in connection with the description of the compounds of the formula (I) according to the invention.

Examples of the compounds of the formulae (XIA) and (XIB) are listed in Table 2 below. The meanings of the variables $R^4$, X, Y and Z, each of which is indicated line by line for individual examples, in each individual case stand for the isomers of the formula (XIA) and the formula (XIB)

TABLE 2

| Examples of the compounds of the formulae (XIA) and (XIB) | | | |
|---|---|---|---|
| $R^4$ | X | Y | Z |
| $CH_3$ | H | CH | $C-CH_3$ |
| $CH_3$ | N | CH | $C-OCH_3$ |
| $CH_3$ | N | CH | $C-OC_2H_5$ |
| $OCH_3$ | N | CH | $C-OCH_3$ |
| $OCH_3$ | N | CH | $C-Cl$ |
| H | N | CH | $C-CH_3$ |
| $CF_3$ | N | CH | $C-OCH_3$ |
| $OCH_3$ | N | CH | $C-OCHF_2$ |
| $CH_3$ | N | CH | $C-OCHF_2$ |
| $OCHF_2$ | N | CH | $C-OCHF_2$ |
| $CH_3$ | N | N | $C-CH_3$ |
| $CH_3$ | N | N | $C-OCH_3$ |
| $OCH_3$ | N | N | $C-OCH_3$ |
| $C_2H_5$ | N | CH | $C-OCH_3$ |
| $C_2H_5$ | N | N | $C-OCH_3$ |

The aminoguanidines of the formulae (XIA) and (XIB) were hitherto unknown from the literature.

In general, the new compounds of the formulae (XIA) and (XIB) are obtained when azines of the formula (VIII)—above—are reacted with aminoguanidine or an acid salt thereof, such as, for example, the hydrochloride or the hydrogen carbonate, if appropriate in the presence of a diluent, such as, for example, ethanol, acetone, acetonitrile or dimethylformamide, and if appropriate in the presence of a base, such as, for example, potassium carbonate or triethylamine, at temperatures from 0° C. to 100° C.

The aminoguanidines of the formula (XIA) can also be obtained from known S-methyl-isothioureidoazines of the formula (XII)

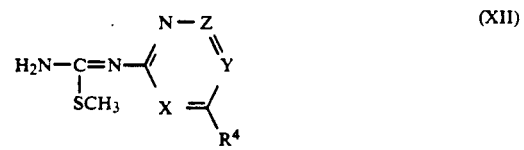

in which
$R^4$, X, Y and Z have the abovementioned meanings, and hydrazine or hydrazine hydrate, if appropriate in the presence of a diluent, such as, for example, ethanol or dioxane, at temperatures from 0° C. to 100° C. (cf. EP-A 117,014/U.S. Pat. No. 4,689,070).

The aminoguanidines of the formula (XIB) can also be obtained by reacting hydrazinoazines of the formula (IX)—above—with cyanamide, if appropriate in the presence of an acid, such as, for example, hydrochloric acid, and if appropriate in the presence of a diluent, such as, for example, ethanol and/or water, at temperatures from 0° C. to 100° C.

Formula (V) provides a general definition of the ester(amide)s also required as intermediates. In formula (V), $R^3$ preferably, or in particular, has the meaning which has already been preferably mentioned above, or mentioned above as particularly preferred, for $R^3$ in connection with the description of the compounds of the formula (I) according to the invention, R preferably stands for $C_1-C_4$-alkyl, in particular for methyl or ethyl, and $Q^1$ preferably stands for $C_1-C_4$-alkoxy or di-$(C_1-C_2)$-alkylamino, in particular for methoxy, ethoxy or dimethylamino.

Examples of the compounds of the formula (V) which may be mentioned are: N,N-dimethylformamide dimethyl acetal and -diethyl acetal, trimethyl orthoformate and triethyl orthoformate, trimethyl orthoacetate and triethyl orthoacetate.

The compounds of the formula (V) are known chemicals for synthesis.

Formula (III) provides a general definition of the sulphonyl halides and sulphonic anhydrides also to be used as starting substances in the process according to the invention for the preparation of the new compounds of the formula (I). In formula (III), $R^1$ preferably, or in particular, has the meaning which has been preferentially mentioned above, or mentioned above as particularly preferred, in context with the description of the compounds of the formula (I) according to the invention, and Q preferably stands for chlorine.

Examples of the starting substances of the formula (III) which may be mentioned are: benzenesulphonyl chloride, 2-chloro-, 3-chloro-, 4-chloro-, 2,5-dichloro-, 2-fluoro-, 4-fluoro-, 2-bromo-, 4-bromo-, 2-cyano-, 4-cyano-, 2-nitro-, 4-nitro-, 2-methyl-, 4-methyl-, 2-chloromethyl-, 2-trifluoromethyl-, 2-methoxy-, 4-methoxy-, 2-methylthio-, 2-trifluoromethylthio-, 2-difluoromethylthio-, 2-cyclopropyloxycarbonyl-, 2-phenoxy-, 2-difluoromethoxy-, 2-trifluoromethoxy-, 2-(2-chloroethoxy)-, 2-methylthiomethyl-, 2-dimethylaminosulphonyl-, 2-phenyl-, 2-methoxycarbonyl-, 2-ethoxycarbonyl-, 2-dimethylaminocarbonyl-and 2-diethylaminocarbonylbenzenesulphonyl chloride and (2-chloro-phenyl)-, (2-cyano-phenyl)-, (2-methoxycarbonyl-phenyl)- and (2-trifluoromethoxy-phenyl)-methanesulphonyl chloride, 2-chloro-6-methyl-benzenesulphonyl chloride and 2,6-dichloro-benzenesulphonyl chloride.

The sulphonyl halides or sulphonic anhydrides of the formula (III) are known and/or can be prepared by processes known per se (cf. J. Org. Chem. 33 (1968), 2104; J. Org. Chem. 25 (1960), 1824; DE-AS (German Published Specification) 2,308,262; EP-OS (European Published Specifications) 23,140, 23,141, 23,422, 35,893, 48,143, 51,466, 64,322, 70,041, 44,808 and 44,809; U.S. Pat. Nos. 2,929,820, 4,282,242; 4,348,220 and 4,372,778 and Angew. Chem. 93 (1981), 151).

The process (a) according to the invention for the preparation of the new compounds of the formula (I) is preferably carried out using diluents. Suitable diluents in this process are virtually all inert organic solvents. These preferably include aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether and dibutyl ether, glycol dimethyl ether, diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, amides, such as, for example, dimethylformamide, dimethylacetamide and N-methyl-pyrrolidone, and also dimethyl sulphoxide, tetramethylene sulphone, hexamethylphosphoric triamide and pyridine.

Acid acceptors which can be employed in the process (a) according to the invention include all the acidbinding agents which can customarily be used for reactions of this type. Alkali metal hydroxides, such as, for example, sodium hydroxide and potassium hydroxide, alkaline earth metal hydroxides, such as, for example, calcium hydroxide, alkali metal carbonates and alkali metal alkoxides, such as sodium carbonate and potassium carbonate, sodium tert.-butoxide and potassium tert.-butoxide, furthermore aliphatic, aromatic or heterocyclic amines, for example triethylamine, trimethylamine, dimethylaniline, dimethylbenzylamine, pyridine, picoline, 1,5-diazabicyclo-[4,3,0]-non-5-ene (DBN), 1,8-diazabicyclo-[5,4,0]-undec-7-ene (DBU) and 1,4-diazabicyclo[2,2,2]-octane (DABCO) are preferably suitable.

Catalysts which can be used in the process according to the invention are metal halides, such as, for example, aluminum chloride or zinc chloride.

When carrying out process (a) according to the invention, the reaction temperatures can be varied within a relatively wide range. In general, the process is carried out at temperatures from $-50°$ C. to $+50°$ C., preferably at temperatures from $-40°$ C. to $+40°$ C.

For carrying out process (a) according to the invention, 1 to 5 moles, preferably 1 to 4 moles, of sulphonyl halide or sulphonic anhydride of the formula (III) are generally employed per mole of aminoazole of the formula (II). If disulphonylated compounds of the formula $(I, R^2 = -SO_2-R^1)$ are to be prepared in a one-pot reaction, at least 2 moles of sulphonyl halide or sulphonic anhydride (III) are to be employed per mole of aminoazole (II).

The reactants can be combined in any desired sequence. In a preferred embodiment of the process according to the invention, the starting substances of the formulae (II) and (III) are stirred at room temperature with a diluent, the mixture is cooled, if appropriate, and the acid acceptor is slowly metered into this mixture. The reaction mixture is then stirred until the reaction is complete.

If appropriate, the mixture is concentrated and/or diluted with a virtually water-immiscible organic solvent, such as, for example, methylene chloride, and working up can be carried out in a customary manner, for example by washing with water, drying, filtering and carefully removing the solvent from the filtrate by distillation. The crude product which remains in the residue can be purified further in a customary manner, for example by column chromatography and/or recrystallization.

The compounds which can be obtained as described above, of the formula (I) in which $R^2$ stands for the grouping $-SO_2-R^1$, can be reacted to give compounds of the formula (I) in which $R^2$ stands for hydrogen by a reaction with desulphonylating agents, if appropriate in the presence of diluents.

In this connections, desulphonylating agents are taken to mean substances which are able to eliminate a sulphonyl grouping from N,N-bis-sulphonyl-amino compounds. Suitable desulphonylation agents are, above all, alkali metal hydroxides or alkaline earth metal hydroxides, such as sodium hydroxide, potassium hydroxide and calcium hydroxide, alkali metal alkoxides, such as sodium methoxide, potassium methoxide, sodium ethoxide and potassium ethoxide, furthermore ammonia, alkylamines, such as methylamine, ethylamine, propylamine and butylamine, and also dialkylamines, such as dimethylamine and diethylamine. Ammonia is preferably employed as a desulphonylating agent.

The desulphonylation is preferably carried out in the presence of diluents. Apart from water, preferred diluents are polar organic solvents, such as methanol, ethanol, propanol, isopropanol, 2-methoxyethanol, 2-ethoxyethanol and dioxane.

The desulphonylation is generally carried out at temperatures from 0° C. to 150° C., preferably at temperatures from 20° C. to 100° C.

For desulphonylation, the reactants are generally mixed at room temperature and, if appropriate, stirred at an increased temperature until the reaction is complete. If appropriate for working up, the mixture is concentrated, diluted with water and acidified with a strong acid, such as, for example, hydrochloric acid. During this process, the product (I, $R^2=H$) is obtained in the form of crystals and can be isolated by filtering off with suction.

Formulae (IVA) and (IVB) provide general definitions of the sulphonylated aminoguanidines to be used as starting substances in process (b) according to the invention for the preparation of compounds of the formula (I).

In the formulae (IVA) and (IVB), $R^1$, $R^4$, X, Y and Z preferably, or in particular, have those meanings which have already been preferably mentioned above, or mentioned above as particularly preferred, for $R^1$, $R^4$, X, Y and Z in connection with the description of the compounds of the formula (I) according to the invention.

Examples of the starting substances of the formulae (IVA) and (IVB) are listed in Table 3 below.

The meanings of the variables $R^1$, $R^4$, X, Y and Z, each of which is indicated line by line for individual examples, in each individual case stand for the isomers of the formulae (IVA) and (IVB).

TABLE 3

| Examples of the compounds of the formulae (IVA) and (IVB) | | | | |
|---|---|---|---|---|
| $R^1$ | $R^4$ | X | Y | Z |
| 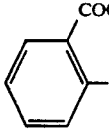 COOCH$_3$ | CH$_3$ | N | CH | C—CH$_3$ |
| 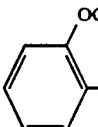 COOCH$_3$ | CH$_3$ | N | CH | C—CH$_3$ |
| 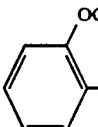 Cl | CH$_3$ | N | CH | C—CH$_3$ |
| 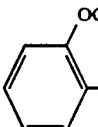 COOC$_2$H$_5$ | CH$_3$ | N | CH | C—CH$_3$ |
| 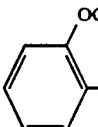 F | CH$_3$ | N | CH | C—CH$_3$ |

TABLE 3-continued

| Examples of the compounds of the formulae (IVA) and (IVB) | | | | |
|---|---|---|---|---|
| $R^1$ | $R^4$ | X | Y | Z |
| 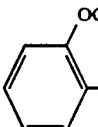 Br | CH$_3$ | N | CH | C—CH$_3$ |
| 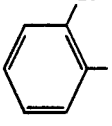 CF$_3$ | CH$_3$ | N | CH | C—CH$_3$ |
| 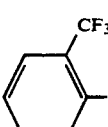 CH$_3$ | CH$_3$ | N | CH | C—CH$_3$ |
| 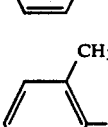 OCH$_3$ | CH$_3$ | N | CH | C—CH$_3$ |
| 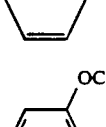 OCHF$_2$ | CH$_3$ | N | CH | C—CH$_3$ |
| 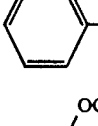 OCF$_3$ | CH$_3$ | N | CH | C—CH$_3$ |
| 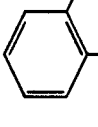 OCH$_2$CH$_2$Cl | CH$_3$ | N | CH | C—CH$_3$ |
| 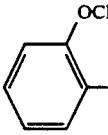 SCH$_3$ | CH$_3$ | N | CH | C—CH$_3$ |
| 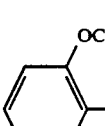 SO$_2$CH$_3$ | CH$_3$ | N | CH | C—CH$_3$ |
| 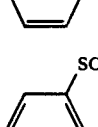 SO$_2$N(CH$_3$)$_2$ | CH$_3$ | N | CH | C—CH$_3$ |
| 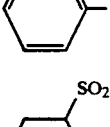 COOCH$_3$ | CH$_3$ | N | CH | C—OCH$_3$ |

TABLE 3-continued
Examples of the compounds of the formulae (IVA) and (IVB)

| R¹ | R⁴ | X | Y | Z |
|---|---|---|---|---|
| 2-(COOC₂H₅)-phenyl | CH₃ | N | CH | C—OCH₃ |
| 2-Cl-phenyl | CH₃ | N | CH | C—OCH₃ |
| 2-F-phenyl | CH₃ | N | CH | C—OCH₃ |
| 2-Br-phenyl | CH₃ | N | CH | C—OCH₃ |
| 2-CF₃-phenyl | CH₃ | N | CH | C—OCH₃ |
| 2-OCHF₂-phenyl | CH₃ | N | CH | C—OCH₃ |
| 2-OCF₃-phenyl | CH₃ | N | CH | C—OCH₃ |
| 2-(OCH₂CH₂Cl)-phenyl | CH₃ | N | CH | C—OCH₃ |
| 3-methyl-2-(COOCH₃)-thienyl | CH₃ | N | CH | C—OCH₃ |
| 2-SCH₃-phenyl | CH₃ | N | CH | C—OCH₃ |
| 2-SO₂CH₃-phenyl | CH₃ | N | CH | C—OCH₃ |
| 2-SO₂N(CH₃)₂-phenyl | CH₃ | N | CH | C—OCH₃ |
| 2-(COOCH₃)-phenyl | OCH₃ | N | CH | C—OCH₃ |
| 2-(COOC₂H₅)-phenyl | OCH₃ | N | CH | C—OCH₃ |
| 2-(COOCH₃)-benzyl | OCH₃ | N | CH | C—OCH₃ |
| 2-(COOC₂H₅)-benzyl | OCH₃ | N | CH | C—OCH₃ |
| 3-methyl-2-(COOCH₃)-thienyl | OCH₃ | N | CH | C—OCH₃ |
| 2-Cl-phenyl | OCH₃ | N | CH | C—OCH₃ |
| 2-F-phenyl | OCH₃ | N | CH | C—OCH₃ |
| 2-Br-phenyl | OCH₃ | N | CH | C—OCH₃ |
| 2-CF₃-phenyl | OCH₃ | N | CH | C—OCH₃ |
| 2-OCHF₂-phenyl | OCH₃ | N | CH | C—OCH₃ |

TABLE 3-continued

Examples of the compounds of the formulae (IVA) and (IVB)

| R¹ | R⁴ | X | Y | Z |
|---|---|---|---|---|
| 2-(OCF₃)-phenyl | OCH₃ | N | CH | C—OCH₃ |
| 2-(OCH₂CH₂Cl)-phenyl | OCH₃ | N | CH | C—OCH₃ |
| 2-(SCH₃)-phenyl | OCH₃ | N | CH | C—OCH₃ |
| 2-(SO₂CH₃)-phenyl | OCH₃ | N | CH | C—OCH₃ |
| 2-(C₆H₅)-phenyl | OCH₃ | N | CH | C—OCH₃ |
| 2-(OC₆H₅)-phenyl | OCH₃ | N | CH | C—OCH₃ |
| 2-(SO₂N(CH₃)₂)-phenyl | OCH₃ | N | CH | C—OCH₃ |
| 2-(SO₂—N(OCH₃)(CH₃))-phenyl | OCH₃ | N | CH | C—OCH₃ |
| 2-(COOCH₃)-phenyl | CF₃ | N | CH | C—OCH₃ |
| 2-(COOC₂H₅)-phenyl | CF₃ | N | CH | C—OCH₃ |
| 2-Cl-phenyl | CF₃ | N | CH | C—OCH₃ |
| 2-F-phenyl | CF₃ | N | CH | C—OCH₃ |
| 2-Br-phenyl | CF₃ | N | CH | C—OCH₃ |
| 2-(CF₃)-phenyl | CF₃ | N | CH | C—OCH₃ |
| 3-methyl-2-(COOCH₃)-thien-yl | CF₃ | N | CH | C—OCH₃ |
| 2-(OCHF₂)-phenyl | CF₃ | N | CH | C—OCH₃ |
| 2-(OCF₃)-phenyl | CF₃ | N | CH | C—OCH₃ |
| 2-(OCH₂CH₂Cl)-phenyl | CF₃ | N | CH | C—OCH₃ |
| 2-(SCH₃)-phenyl | CF₃ | N | CH | C—OCH₃ |
| 2-(SO₂CH₃)-phenyl | CF₃ | N | CH | C—OCH₃ |
| 2-(SO₂N(CH₃)₂)-phenyl | CF₃ | N | CH | C—OCH₃ |

TABLE 3-continued

Examples of the compounds of the formulae (IVA) and (IVB)

| R¹ | R⁴ | X | Y | Z |
|---|---|---|---|---|
| 2-(COOCH₃)-benzyl (CH₂–) | CF₃ | N | CH | C—OCH₃ |
| 2-(OCHF₂)-benzyl (CH₂–) | CF₃ | N | CH | C—OCH₃ |
| 2-(OCF₃)-benzyl (CH₂–) | CF₃ | N | CH | C—OCH₃ |
| 2-(OCHF₂)-benzyl (CH₂–) | CH₃ | N | CH | C—OCH₃ |
| 2-(OCF₃)-benzyl (CH₂–) | CH₃ | N | CH | C—OCH₃ |
| 2-(OCHF₂)-benzyl (CH₂–) | OCH₃ | N | CH | C—OCH₃ |
| 2-(OCF₃)-benzyl (CH₂–) | OCH₃ | N | CH | C—OCH₃ |
| 2-(COOCH₃)-phenyl | OCH₃ | N | CH | C—Cl |
| 2-(COOC₂H₅)-phenyl | OCH₃ | N | CH | C—Cl |
| 2-(COOCH₃)-benzyl (CH₂–) | OCH₃ | N | CH | C—Cl |
| 2-(COOC₂H₅)-benzyl (CH₂–) | OCH₃ | N | CH | C—Cl |
| 2-Cl-phenyl | OCH₃ | N | CH | C—Cl |
| 2-F-phenyl | OCH₃ | N | CH | C—Cl |
| 2-Br-phenyl | OCH₃ | N | CH | C—Cl |
| 2-CF₃-phenyl | OCH₃ | N | CH | C—Cl |
| 2-OCHF₂-phenyl | OCH₃ | N | CH | C—Cl |
| 2-OCF₃-phenyl | OCH₃ | N | CH | C—Cl |
| 2-(OCHF₂)-benzyl (CH₂–) | OCH₃ | N | CH | C—Cl |
| 2-(OCF₃)-benzyl (CH₂–) | OCH₃ | N | CH | C—Cl |
| 2-(OCH₂CH₂Cl)-phenyl | OCH₃ | N | CH | C—Cl |
| 2-(SCH₃)-phenyl | OCH₃ | N | CH | C—Cl |

TABLE 3-continued

Examples of the compounds of the formulae (IVA) and (IVB)

| R¹ | R⁴ | X | Y | Z |
|---|---|---|---|---|
| 2-(SO₂CH₃)-phenyl | OCH₃ | N | CH | C—Cl |
| 2-(SO₂N(CH₃)₂)-phenyl | OCH₃ | N | CH | C—Cl |
| 2-(COOCH₃)-phenyl | CH₃ | N | CH | C—OCHF₂ |
| 2-(COOC₂H₅)-phenyl | CH₃ | N | CH | C—OCHF₂ |
| 2-Cl-phenyl | CH₃ | N | CH | C—OCHF₂ |
| 2-F-phenyl | CH₃ | N | CH | C—OCHF₂ |
| 2-Br-phenyl | CH₃ | N | CH | C—OCHF₂ |
| 2-CF₃-phenyl | CH₃ | N | CH | C—OCHF₂ |
| 2-OCHF₂-phenyl | CH₃ | N | CH | C—OCHF₂ |
| 2-OCF₃-phenyl | CH₃ | N | CH | C—OCHF₂ |
| 2-OCH₂CH₂Cl-phenyl | CH₃ | N | CH | C—OCHF₂ |
| 3-methyl-2-(COOCH₃)-thienyl | CH₃ | N | CH | C—OCHF₂ |
| 3-methyl-2-(COOCH₃)-thienyl | OCH₃ | N | CH | C—Cl |
| 3-methyl-2-(COOCH₃)-thienyl | OCH₃ | N | CH | C—OCHF₂ |
| 2-(SCH₃)-phenyl | CH₃ | N | CH | C—OCHF₂ |
| 2-(SO₂CH₃)-phenyl | CH₃ | N | CH | C—OCHF₂ |
| 2-(SO₂N(CH₃)₂)-phenyl | CH₃ | N | CH | C—OCHF₂ |
| 2-(COOCH₃)-phenyl | OCH₃ | N | CH | C—OCHF₂ |
| 2-(COOC₂H₅)-phenyl | OCH₃ | N | CH | C—OCHF₂ |
| 2-(COOCH₃)-benzyl | OCH₃ | N | CH | C—OCHF₂ |
| 2-(COOC₂H₅)-benzyl | OCH₃ | N | CH | C—OCHF₂ |
| 2-CF₃-phenyl | OCH₃ | N | CH | C—OCHF₂ |

TABLE 3-continued

Examples of the compounds of the formulae (IVA) and (IVB)

| R¹ | R⁴ | X | Y | Z |
|---|---|---|---|---|
| 2-Cl-phenyl | OCH₃ | N | CH | C—OCHF₂ |
| 2-F-phenyl | OCH₃ | N | CH | C—OCHF₂ |
| 2-Br-phenyl | OCH₃ | N | CH | C—OCHF₂ |
| 2-OCHF₂-phenyl | OCH₃ | N | CH | C—OCHF₂ |
| 2-OCF₃-phenyl | OCH₃ | N | CH | C—OCHF₂ |
| 2-SCH₃-phenyl | OCH₃ | N | CH | C—OCHF₂ |
| 2-SO₂CH₃-phenyl | OCH₃ | N | CH | C—OCHF₂ |
| 2-SO₂N(CH₃)₂-phenyl | OCH₃ | N | CH | C—OCHF₂ |
| 2-COOCH₃-phenyl | OCHF₂ | N | CH | C—OCHF₂ |
| 2-COOC₂H₅-phenyl | OCHF₂ | N | CH | C—OCHF₂ |
| 2-COOCH₃-phenyl-CH₂— | OCHF₂ | N | CH | C—OCHF₂ |
| 2-COOC₂H₅-phenyl-CH₂— | OCHF₂ | N | CH | C—OCHF₂ |
| 2-Cl-phenyl | OCHF₂ | N | CH | C—OCHF₂ |
| 2-F-phenyl | OCHF₂ | N | CH | C—OCHF₂ |
| 2-Br-phenyl | OCHF₂ | N | CH | C—OCHF₂ |
| 2-CF₃-phenyl | OCHF₂ | N | CH | C—OCHF₂ |
| 2-OCHF₂-phenyl | OCHF₂ | N | CH | C—OCHF₂ |
| 2-OCF₃-phenyl | OCHF₂ | N | CH | C—OCHF₂ |
| 2-OCHF₂-phenyl-CH₂— | OCHF₂ | N | CH | C—OCHF₂ |
| 2-OCF₃-phenyl-CH₂— | OCHF₂ | N | CH | C—OCHF₂ |
| 3-COOCH₃-thien-2-yl | OCHF₂ | N | CH | C—OCHF₂ |
| 2-OCH₂CH₂Cl-phenyl | OCHF₂ | N | CH | C—OCHF₂ |

TABLE 3-continued

Examples of the compounds of the formulae (IVA) and (IVB)

| R¹ | R⁴ | X | Y | Z |
|---|---|---|---|---|
| 2-(SCH₃)C₆H₄– | OCHF₂ | N | CH | C—OCHF₂ |
| 2-(SO₂CH₃)C₆H₄– | OCHF₂ | N | CH | C—OCHF₂ |
| 2-(SO₂N(CH₃)₂)C₆H₄– | OCHF₂ | N | CH | C—OCHF₂ |
| 2-(C₆H₅)C₆H₄– | OCHF₂ | N | CH | C—OCHF₂ |
| 2-(COOCH₃)C₆H₄– | CH₃ | N | N | C—CH₃ |
| 3-(COOCH₃)thien-2-yl | CH₃ | N | N | C—CH₃ |
| 2-(Cl)C₆H₄– | CH₃ | N | N | C—CH₃ |
| 2-(COOCH₃)C₆H₄– | CH₃ | N | N | C—OCH₃ |
| 2-(COOC₂H₅)C₆H₄– | CH₃ | N | N | C—OCH₃ |
| 3-(COOCH₃)thien-2-yl | CH₃ | N | N | C—OCH₃ |
| 2-(Cl)C₆H₄– | CH₃ | N | N | C—OCH₃ |
| 2-(F)C₆H₄– | CH₃ | N | N | C—OCH₃ |
| 2-(Br)C₆H₄– | CH₃ | N | N | C—OCH₃ |
| 2-(CF₃)C₆H₄– | CH₃ | N | N | C—OCH₃ |
| 2-(OCHF₂)C₆H₄– | CH₃ | N | N | C—OCH₃ |
| 2-(OCF₃)C₆H₄– | CH₃ | N | N | C—OCH₃ |
| 2-(OCH₂CH₂Cl)C₆H₄– | CH₃ | N | N | C—OCH₃ |
| 2-(SCH₃)C₆H₄– | CH₃ | N | N | C—OCH₃ |
| 2-(SO₂CH₃)C₆H₄– | CH₃ | N | N | C—OCH₃ |
| 2-(SO₂N(CH₃)₂)C₆H₄– | CH₃ | N | N | C—OCH₃ |
| 2-(COOCH₃)C₆H₄–CH₂– | CH₃ | N | N | C—OCH₃ |
| 2-(OCHF₂)C₆H₄–CH₂– | CH₃ | N | N | C—OCH₃ |

TABLE 3-continued

Examples of the compounds of the formulae (IVA) and (IVB)

| R¹ | R⁴ | X | Y | Z |
|---|---|---|---|---|
| 2-(OCF₃)benzyl | CH₃ | N | N | C—OCH₃ |
| 2-(COOCH₃)phenyl | OCH₃ | N | N | C—OCH₃ |
| 2-(COOC₂H₅)phenyl | OCH₃ | N | N | C—OCH₃ |
| 2-(COOCH₃)benzyl | OCH₃ | N | N | C—OCH₃ |
| 2-(OCHF₂)benzyl | OCH₃ | N | N | C—OCH₃ |
| 3-methyl-2-(COOCH₃)thienyl | OCH₃ | N | N | C—OCH₃ |
| 2-Cl-phenyl | OCH₃ | N | N | C—OCH₃ |
| 2-F-phenyl | OCH₃ | N | N | C—OCH₃ |
| 2-Br-phenyl | OCH₃ | N | N | C—OCH₃ |
| 2-CF₃-phenyl | OCH₃ | N | N | C—OCH₃ |
| 2-OCHF₂-phenyl | OCH₃ | N | N | C—OCH₃ |
| 2-(OCHF₂)benzyl | OCH₃ | N | N | C—OCH₃ |
| 2-OCF₃-phenyl | OCH₃ | N | N | C—OCH₃ |
| 2-(OCF₃)benzyl | OCH₃ | N | N | C—OCH₃ |
| 2-(OCH₂CH₂Cl)phenyl | OCH₃ | N | N | C—OCH₃ |
| 2-SCH₃-phenyl | OCH₃ | N | N | C—OCH₃ |
| 2-SO₂CH₃-phenyl | OCH₃ | N | N | C—OCH₃ |
| 2-SO₂N(CH₃)₂-phenyl | OCH₃ | N | N | C—OCH₃ |
| 2-(COOCH₃)phenyl | C₂H₅ | N | N | C—OCH₃ |
| 2-(COOCH₃)phenyl | CH₃ | N | N | C—OC₂H₅ |
| 2-(COOCH₃)phenyl | OCH₃ | N | N | C—NHC₂H₅ |

TABLE 3-continued

Examples of the compounds of the formulae (IVA) and (IVB)

| R¹ | R⁴ | X | Y | Z |
|---|---|---|---|---|
| 2-COOCH₃-phenyl | OC₂H₅ | N | N | C—NHCH₃ |
| 1-methyl-5-COOCH₃-pyrazol-3-yl | OCH₃ | N | CH | C—OCH₃ |
| 1-methyl-5-COOC₂H₅-pyrazol-3-yl | OCH₃ | N | CH | C—OCH₃ |
| 1-methyl-5-COOCH₃-pyrazol-3-yl | OCH₃ | N | N | C—OCH₃ |
| 1-methyl-5-COOC₂H₅-pyrazol-3-yl | OCH₃ | N | N | C—OCH₃ |
| 3-Cl-isothiazol-4-yl | OCH₃ | N | CH | C—OCH₃ |
| 3-Cl-isothiazol-4-yl | OCH₃ | N | N | C—OCH₃ |
| 2-COOCH(CH₃)₂-4-Cl-phenyl | OCH₃ | N | N | C—OCH₃ |
| 2-COOC₂H₅-5-OCHF₂-phenyl | OCH₃ | N | CH | C—OCH₃ |
| 3-CF₃-pyridin-2-yl | OCH₃ | N | CH | C—OCH₃ |
| 2-CH₃-6-Cl-phenyl | OCH₃ | N | CH | C—OCH₃ |
| 2-OCH₂CH₂OCH₃-phenyl | OCH₃ | N | CH | C—OCH₃ |
| 2-OCH₂CH₂OCH₃-phenyl | OCH₃ | N | N | C—OCH₃ |

Some of the sulphonylated aminoguanidines of the formula (IVA) are disclosed in EP-A 224,078 and U.S. Pat. No. 4,725,303, and some of them form the subject of a German Patent Application P 3,818,040.5 filed May 27, 1988.

The compounds of the general formula (IVA) are obtained when sulphonyl compounds of the general formula (XIII)

$$R^1-SO_2-N=C-NH-\underset{Q^4}{\overset{N-Z}{\underset{X}{\bigg|}}}\!\!\!\diagdown_{R^4}^{Y} \quad (XIII)$$

in which
R¹, R⁴, X, Y and Z have the abovementioned meanings and
Q⁴ stands for halogen or for one of the leaving groups $$R^{34}-SO_2-N-O-R^{35} \quad \text{or} \quad -Q^5-R^{36}$$

which are indicated below, wherein
R³⁴ has the meaning mentioned above for R¹, but is not necessarily identical to R¹ in each individual case,
R³⁵ stands for alkyl, alkenyl or aralkyl,
R³⁶ stands for in each case optionally substituted alkyl, aralkyl or aryl and
Q⁵ stands for oxygen or sulphur with hydrazine or a hydrazine/water adduct or hydrazine/acid adduct, if appropriate in the presence of an acid acceptor, such as, for example, potassium carbonate, and if appropriate in the presence of a diluent, such as, for example, methanol, ethanol and/or water, at temperatures from −20° C. to +100° C.

Some of the compounds of the formula (IVA) can also be obtained as outlined below (R as mentioned above for R¹⁰)

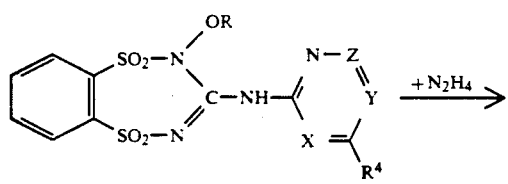

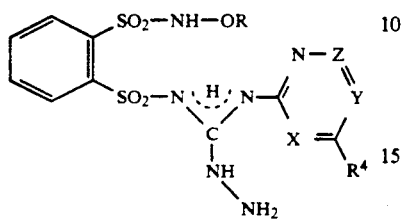

(for the principle of the reaction, cf. U.S. Pat. No. 4,659,364, EP-A 173,319).

Formula (XIII) provides a general definition of the sulphonyl compounds required as intermediates. In formula (XIII), $R^1$, $R^4$, X, Y and Z preferably, or in particular, have those meanings which have already been preferably mentioned above, or mentioned above as particularly preferred, for $R^1$, $R^4$, X, Y and Z in context with the description of the compounds of the formula (I) according to the invention and $Q^4$ preferably stands for chlorine or one of the leaving groups

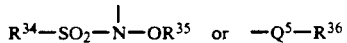

mentioned below, wherein $R^{34}$ has the meaning preferably given above for $R^1$, but is not necessarily identical to $R^1$ in each individual case, $R^{35}$ stands for $C_1$-$C_4$-alkyl, $C_3$-$C_4$-alkenyl or benzyl, $R^{36}$ stands for $C_1$-$C_4$-alkyl which is optionally substituted by carboxyl, $C_1$-$C_4$-alkoxycarbonyl or $C_1$-$C_4$-alkoxy or for benzyl or phenyl, each of which is optionally substituted by fluorine, chlorine, bromine, $C_1$-$C_4$-alkyl or $C_1$-$C_4$-alkoxy, and $Q^5$ stands for oxygen or sulphur.

Examples of the compounds of the formula (XIII) are listed in Table 4 below.

TABLE 4

Examples of the compounds of the formula (XIII)

| $Q^4$ | $R^1$ | $R^4$ | X | Y | Z |
|---|---|---|---|---|---|
| 2-Cl-C₆H₄-SO₂-N(OCH₃)- | Cl (2-position on phenyl) | CH₃ | N | CH | C—OCH₃ |
| 2-Br-C₆H₄-SO₂-N(OCH₃)- | Br (2-position on phenyl) | OCH₃ | N | CH | C—OCH₃ |
| 2-F-C₆H₄-SO₂-N(OCH₃)- | F (2-position on phenyl) | OCH₃ | N | CH | C—OCH₃ |
| 2-CF₃-C₆H₄-SO₂-N(OCH₃)- | CF₃ (2-position on phenyl) | OCH₃ | N | CH | C—OCH₃ |
| 2-OCHF₂-C₆H₄-SO₂-N(OCH₃)- | OCHF₂ (2-position on phenyl) | OCH₃ | N | CH | C—OCH₃ |
| 2-OCF₃-C₆H₄-SO₂-N(OCH₃)- | OCF₃ (2-position on phenyl) | OCH₃ | N | CH | C—OCH₃ |

TABLE 4-continued
Examples of the compounds of the formula (XIII)
| Q⁴ | R¹ | R⁴ | X | Y | Z |
|---|---|---|---|---|---|
| 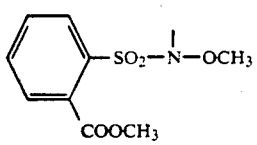 | 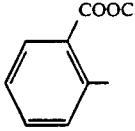 | $CH_3$ | N | CH | $C-CH_3$ |
| 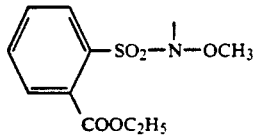 | 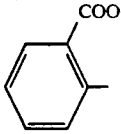 | $CH_3$ | N | CH | $C-CH_3$ |
| 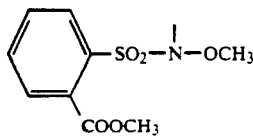 | 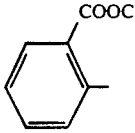 | $OCH_3$ | N | CH | $C-OCH_3$ |
| 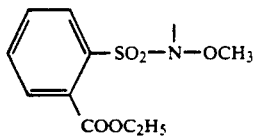 | 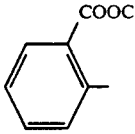 | $OCH_3$ | N | CH | $C-OCH_3$ |
| 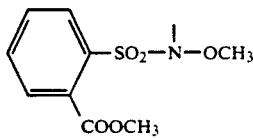 | 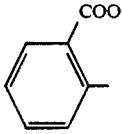 | $C_2H_5$ | N | CH | $C-OCH_3$ |
| 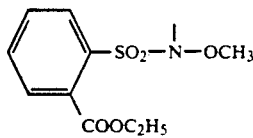 | 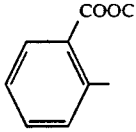 | $C_2H_5$ | N | CH | $C-OCH_3$ |
| 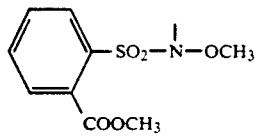 | 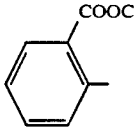 | $OCH_3$ | N | CH | $C-Cl$ |
| 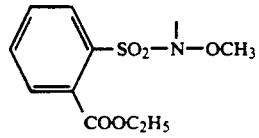 | 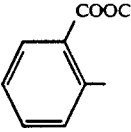 | $OCH_3$ | N | CH | $C-Cl$ |
| 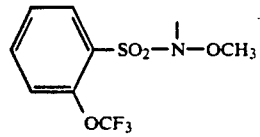 | 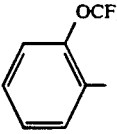 | $OCH_3$ | N | CH | $C-Cl$ |
| 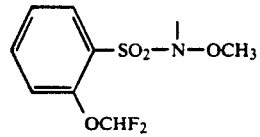 | 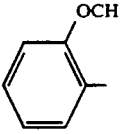 | $OCH_3$ | N | CH | $C-Cl$ |

TABLE 4-continued

Examples of the compounds of the formula (XIII)

| $Q^4$ | $R^1$ | $R^4$ | X | Y | Z |
|---|---|---|---|---|---|
| 2-(SO$_2$-N(OCH$_3$))-, 1-(SO$_2$-CH$_3$)-phenyl | 2-(SO$_2$-CH$_3$)-phenyl | H | N | CH | C—CH$_3$ |
| 2-(SO$_2$-N(OCH$_3$))-, 1-(SO$_2$-N(CH$_3$)$_2$)-phenyl | 2-(SO$_2$-N(CH$_3$)$_2$)-phenyl | CH$_3$ | N | CH | C—OCH$_3$ |
| 2-(SO$_2$-N(OCH$_3$))-, 1-(CH$_3$)-phenyl | 2-(CH$_3$)-phenyl | OCH$_3$ | N | CH | C—OCH$_3$ |
| 2-(SO$_2$-N(OCH$_3$))-, 1-(OCH$_3$)-phenyl | 2-(OCH$_3$)-phenyl | CH$_3$ | N | CH | C—OCH$_3$ |
| 2-(SO$_2$-N(OCH$_3$))-, 1-(SCH$_3$)-phenyl | 2-(SCH$_3$)-phenyl | OCH$_3$ | N | CH | C—OCH$_3$ |
| 2-(SO$_2$-N(OCH$_3$))-, 1-(SO$_2$-N(OCH$_3$)(CH$_3$))-phenyl | 2-(SO$_2$-N(OCH$_3$)(CH$_3$))-phenyl | OCH$_3$ | N | CH | C—OCH$_3$ |
| 2-(SO$_2$-N(OCH$_3$))-, 1-(COOCH$_3$)-phenyl | 2-(COOCH$_3$)-phenyl | CH$_3$ | N | CH | C—OC$_2$H$_5$ |
| 2-(SO$_2$-N(OCH$_3$))-, 1-(COOCH$_3$)-phenyl | 2-(COOCH$_3$)-phenyl | OCHF$_2$ | N | CH | C—CH$_3$ |
| 2-(SO$_2$-N(OCH$_3$))-, 1-(Br)-phenyl | 2-(Br)-phenyl | CH$_3$ | N | CH | C—SCH$_3$ |
| 2-(SO$_2$-N(OCH$_3$))-, 1-(CF$_3$)-phenyl | 2-(CF$_3$)-phenyl | CH$_3$ | N | CH | C—N(CH$_3$)$_2$ |

TABLE 4-continued
Examples of the compounds of the formula (XIII)
| Q⁴ | R¹ | R⁴ | X | Y | Z |
|---|---|---|---|---|---|
| 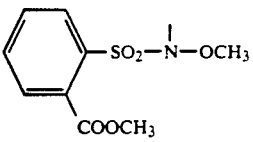 | 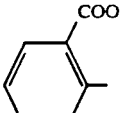 COOCH₃ | OCHF₂ | N | CH | C—OCHF₂ |
| 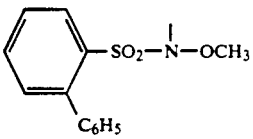 | 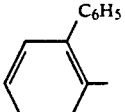 C₆H₅ | OCH₃ | N | CH | C—OCH₃ |
| 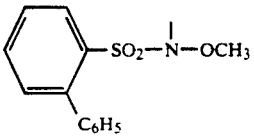 | 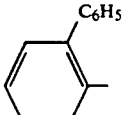 C₆H₅ | OCH₃ | N | N | C—OCH₃ |
| 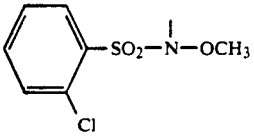 | 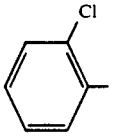 Cl | CH₃ | N | N | C—OCH₃ |
| 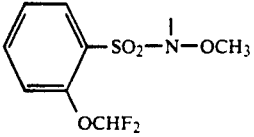 | 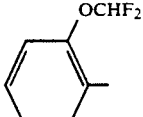 OCHF₂ | OCH₃ | N | N | C—OCH₃ |
| 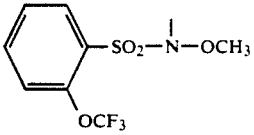 | 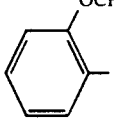 OCF₃ | OCH₃ | N | N | C—OCH₃ |
| 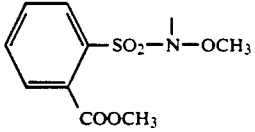 | 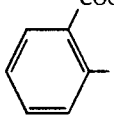 COOCH₃ | CH₃ | N | N | C—OCH₃ |
| 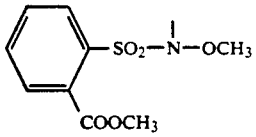 | 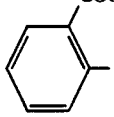 COOCH₃ | OCH₃ | N | N | C—OCH₃ |
| 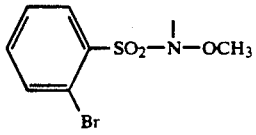 | 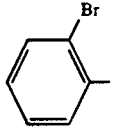 Br | CH₃ | N | N | C—CH₃ |
| 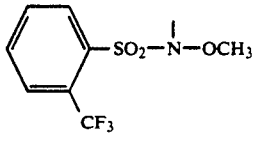 | 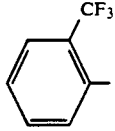 CF₃ | CH₃ | N | N | C—Cl |

TABLE 4-continued
Examples of the compounds of the formula (XIII)
| Q⁴ | R¹ | R⁴ | X | Y | Z |
|---|---|---|---|---|---|
| 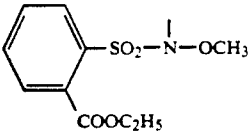 | 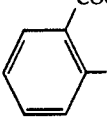 | OCH₃ | N | N | C—OCH₃ |
| 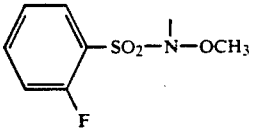 | 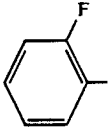 | OCH₃ | N | N | C—OCH₃ |
| 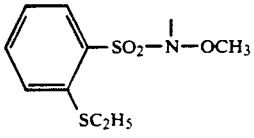 | 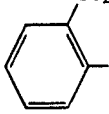 | OCH₃ | N | N | C—OCH₃ |
| 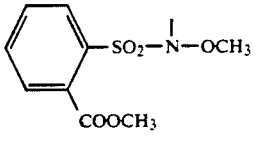 | 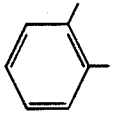 | OCH₃ | N | CH | C—OCH₃ |
| 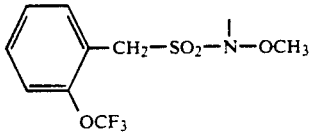 | 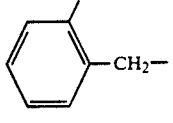 | OCH₃ | N | CH | C—OCH₃ |
| —OC₆H₅ | 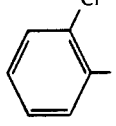 | CH₃ | N | CH | C—CH₃ |
| —OCH₃ | 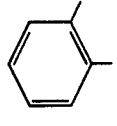 | CH₃ | N | CH | C—OCH₃ |
| —SCH₃ | 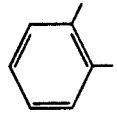 | OCH₃ | N | CH | C—OCH₃ |
| —SC₆H₅ | 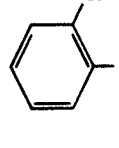 | OCH₃ | N | CH | C—OCH₃ |
| 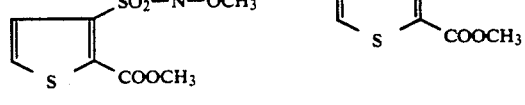 | 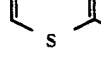 | CH₃ | N | N | C—OCH₃ |

TABLE 4-continued

Examples of the compounds of the formula (XIII)

| $Q^4$ | $R^1$ | $R^4$ | X | Y | Z |
|---|---|---|---|---|---|
| 1-methyl-4-(COOCH₃)-5-(SO₂—N(CH₃)—OCH₃)-pyrazol-3-yl | 1-methyl-4-(COOCH₃)-5-methyl-pyrazol-3-yl | OCH₃ | N | CH | C—OCH₃ |
| 2-(SO₂—N(CH₃)—OCH₃)-phenyl with COOCH₃ | 1-methyl-4-(COOC₂H₅)-5-methyl-pyrazol-3-yl | OCH₃ | N | CH | C—OCH₃ |
| Cl | 2-(COOCH₃)-benzyl (—CH₂—C₆H₄-2-COOCH₃) | OCH₃ | N | CH | C—OCH₃ |
| —OC₆H₅ | 2-(COOCH₃)-benzyl | OCH₃ | N | CH | C—OCH₃ |
| —SC₆H₅ | 2-(COOCH₃)-benzyl | OCH₃ | N | CH | C—OCH₃ |
| Cl | 2-(OCF₃)-phenyl | CH₃ | N | N | C—OCH₃ |
| 2-(OCF₃)-6-(SO₂—N(CH₃)—OCH₃)-phenyl | 2-(OCF₃)-phenyl | CH₃ | N | N | C—OCH₃ |
| O—C₆H₅ | 2-(OCH₂—CH₂—Cl)-phenyl | CH₃ | N | N | C—OCH₃ |
| 2-(OCH₂CH₂Cl)-6-(SO₂—N(CH₃)—OCH₃)-phenyl | 2-(OCH₂CH₂Cl)-phenyl | CH₃ | N | N | C—OCH₃ |
| S—C₆H₅ | 2-(COO—CH(CH₃)₂)-4-Cl-phenyl | CH₃ | N | N | C—OCH₃ |

TABLE 4-continued

| | Examples of the compounds of the formula (XIII) | | | | |
|---|---|---|---|---|---|
| Q⁴ | R¹ | R⁴ | X | Y | Z |
| S—CH₃ | (phenyl substituted with COO—CH(CH₃)₂ and Cl) | CH₃ | N | N | O—CH₃ |
| (phenyl substituted with COOC₂H₅, SO₂—N(OCH₃), and CHF₂O) | (phenyl substituted with COOC₂H₅ and CHF₂O) | OCH₃ | N | CH | O—CH₃ |
| OCH₃ | (phenyl substituted with OCH₂CH₂—OCH₃) | OCH₃ | N | N | O—CH₃ |

The compounds of the formula (XIII) are known and/or can be prepared by processes known per se (cf. EP-A 5,986, EP-A 24,215, EP-A 121,082, EP-A 172,957, EP-A 173,321, EP-A 173,956, EP-A 224,078, DE-OS (German Published Specification) 3,634,928, DE-OS (German Published Specification) 3,634,929).

The sulphonylated aminoguanidines of the formula (IVB) were hitherto unknown from the literature and form the subject of the present invention. The new sulphonylated aminoguanidines of the general formula (IVB) are obtained when their isomer compounds of the formula (IVA)—above—are rearranged by stirring with a polar solvent, such as, for example, methanol, ethanol, propanol, isopropanol and/or water, at temperatures from 0° C. to 150° C.

In order to prepare the compounds of the formula (IVB), it is also possible to generate the isomers of the formula (IVA) as described above and to rearrange them in situ, i.e., without intermediate isolation.

Formula (V) provides a general definition of the ester(amide)s also to be used as starting substances in process (b) according to the invention for the preparation of compounds of the formula (I).

In formula (V), R³ preferably, or in particular, has the meaning which has already been preferably mentioned above, or mentioned above as particularly preferred, for R³ in connection with the description of the compounds of the formula (I) according to the invention, R preferably stands for C₁-C₄-alkyl, in particular for methyl or ethyl, and Q¹ preferably stands for C₁-C₄-alkoxy or di-(C₁-C₂-alkyl)-amino, in particular for methoxy, ethoxy or dimethylamino.

Examples of the starting substances of the formula (V) which may be mentioned are: N,N-dimethylformamide dimethyl acetal and N,N-dimethylformamide diethyl acetal, trimethyl orthoformate and triethyl orthoformate, trimethyl orthoacetate and triethyl orthoacetate.

The compounds of the formula (V) are known chemicals for synthesis.

Process (b) according to the invention is preferably carried out in the presence of a diluent. In addition to the diluents indicated in process (a), alcohols, such as methanol, ethanol, propanol or isopropanol, are also particularly suitable as diluents in process (b).

When carrying out process (b) according to the invention, the reaction temperatures can be varied within a relatively wide range. In general, the process is carried out at temperatures from 0° C. to 150° C., preferably at temperatures from 10° C. to 100° C.

Process (b) according to the invention is generally carried out under atmospheric pressure. However, it is also possible for the process to be carried out under increased or reduced pressure.

For carrying out process (b) according to the invention, the starting substances required in each case are generally employed in approximately equimolar amounts. However, it is also possible to use one of the two components employed in each case in a relatively large excess. The reactions are generally carried out in a suitable diluent, and the reaction mixture is stirred for several hours at the temperature required in each case. Working up in process (b) according to the invention is in each case carried out by customary methods.

Formula (VI) provides a general definition of the substituted aminopyrazolines to be used as starting substances in process (c) according to the invention for the preparation of compounds of the formula (I).

In formula (VI), R⁴, X, Y and Z preferably, or in particular, have those meanings which have already been preferably described above, or described above as particularly preferred, for R⁴, X, Y and Z in connection with the description of the compounds of the formula (I) according to the invention.

Examples of the starting substances of the formula (VI) are listed in Table 5 below.

TABLE 5

| Examples of the compounds of the formula (VI) | | | |
|---|---|---|---|
| R⁴ | X | Y | Z |
| CH₃ | H | CH | C—CH₃ |
| CH₃ | N | CH | C—OCH₃ |
| CH₃ | N | CH | C—OC₂H₅ |
| OCH₃ | N | CH | C—OCH₃ |
| OCH₃ | N | CH | C—Cl |
| H | N | CH | C—CH₃ |

TABLE 5-continued

Examples of the compounds of the formula (VI)

| R⁴ | X | Y | Z |
|---|---|---|---|
| CF₃ | N | CH | C—OCH₃ |
| OCH₃ | N | CH | C—OCHF₂ |
| CH₃ | N | CH | C—OCHF₂ |
| OCHF₂ | N | CH | C—OCHF₂ |
| CH₃ | N | N | C—CH₃ |
| CH₃ | N | N | C—OCH₃ |
| OCH₃ | N | N | C—OCH₃ |
| C₂H₅ | N | CH | C—OCH₃ |
| C₂H₅ | N | N | C—OCH₃ |

The starting substances of the formula (VI) were hitherto unknown from the literature. The compounds of the formula (VI) are obtained when hydrazinoazines of the formula (IX)

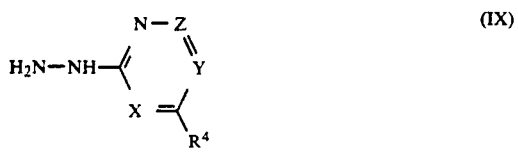

(IX)

in which

R⁴, X, Y and Z have the abovementioned meanings, are reacted with acrylonitrile in the presence of a base, such as, for example, sodium methoxide, potassium methoxide, sodium ethoxide and/or potassium ethoxide, and in the presence of a diluent, such as, for example, methanol and/or ethanol, at temperatures from 0° C. to 100° C.

Furthermore, process (c) according to the invention is carried out using sulphonyl halides or sulphonic anhydrides (III). As far as the starting substances for process (c) are concerned, the data of the compounds of the formula (III) provided above in the description of the starting substances of process (a) are applicable.

Process (c) according to the invention is preferably carried out using diluents.

Suitable diluents are virtually all inert organic solvents, as they have been mentioned above in process (a) according to the invention.

If appropriate, process (c) is carried out in the presence of an acid acceptor. Suitable acid-binding agents are above all those which have been mentioned above in process (a).

When carrying out process (c) according to the invention, the reaction temperatures can be varied within a relatively wide range. In general, the process is carried out at temperatures from −50° C. to +50° C., preferably at temperatures from −40° C. to +40° C.

For carrying out process (c) according to the invention, 1 to 5 moles, preferably 1 to 4 moles, of sulphonyl halide or sulphonic anhydride of the formula (III) are generally employed per mole of aminopyrazoline of the formula (VI). If disulphonylated compounds of the formula (I, R²=—SO₂—R¹) are to be prepared in a one-pot reaction, at least 2 moles of sulphonyl halide or sulphonic anhydride (III) are to be employed per mole of aminopyrazoline (VI).

The reactants can be combined in any desired sequence. In a preferred embodiment of process (c) according to the invention, the starting substances of the formulae (VI) and (III) are stirred at room temperature with a diluent, the mixture is cooled, if appropriate, and the acid acceptor is slowly metered into this mixture. The reaction mixture is then stirred until the reaction is complete.

Working up and (if appropriate) desulphonylation can be carried out as described above in process (a).

If desired, salts can be prepared from the compounds of the general formula (I) according to the invention. Such salts are obtained in a simple manner by customary salt formation methods, for example by dissolving or dispersing a compound of the formula (I) in a suitable solvent, such as, for example, water, methanol, ethanol or acetone, and adding a suitable acid or base. If appropriate, the mixture is stirred for a relatively long time, and the salts can then be isolated by concentrating or filtering off with suction.

The active compounds according to the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example forests, decorative tree plantings, orchards, vineyards, citrus groves, nut orchards, banana platations, coffee plantations, tea plantations, rubber plantations, oil palm plantations, cocoa plantations, soft fruit plantings and hop fields, and for the selective combating of weeds in annual cultures.

The active compounds can be converted to the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkyl naphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silicic acid, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkyl sulphates, arylsulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention, as such or in the form of their formulations, can also be used, for combating weeds, as mixtures with known herbicides, finished formulations or tank mixes being possible.

Possible components for the mixtures are known herbicides, such as, for example, 1-amino-6-ethylthio-3-(2,2-dimethylpropyl)-1,3,5-triazine-2,4(1H,3H)-dione (AMETHYDIONE) or N-(2-benzothiazolyl)-N,N'-dimethyl-urea (METABENZTHIAZURON) for combating weeds in cereals; 4-amino-3-methyl-6-phenyl-1,2,4-triazin-5(4H)-one (METAMITRON) for combating weeds in sugar beets and 4-amino-6-(1,1-dimethylethyl)-3-methylthio-1,2,4-triazin-5(4H)-one (METRIBUZIN) for combating weeds in soy beans; furthermore also 2,4-dichlorophenoxyacetic acid (2,4-D); 4-(2,4-dichlorophenoxy)butyric acid (2,4-DB); 2,4-dichlorophenoxypropionic acid (2,4-DP); 5-(2-chloro-4-trifluoromethyl-phenoxy)-2-nitrobenzoic acid (ACIFLUORFEN); N-(methoxymethyl)-2,6-diethyl-chloroacetanilide (ALACHLOR); methyl 4-aminobenzenesulfonylcarbamate (ASULAM); 2-chloro-4-ethylamino-6-isopropylamino-1,3,5-triazine (ATRAZIN); 3-isopropyl-2,1,3-benzothiadiazin-4-one 2,2-dioxide (BENTAZONE); methyl 5-(2,4-dichlorophenoxy)-2-nitrobenzoate (BIFENOX); 3,5-dibromo-4-hydroxybenzonitrile (BROMOXYNIL); 2,6-dichlorobenzonitrile (DICHLOBENIL); 2-[(2-chlorophenyl)-methyl]-4,4-dimethylisoxazolidin-3-one (DIMETHAZONE); 4-amino-6-t-butyl-3-ethylthio-1,2,4-triazin-5(4H)-one (ETHIOZIN); 2-{4-[(6-chloro-2-benzoxazolyl)-oxy]-phenoxy}-propanoic acid, its methyl ester or its ethyl ester (FENOXAPROP); N,N-dimethyl-N'-(3-trifluoromethylphenyl)-urea (FLUOMETURON); [(4-amino-3,5-dichloro-6-fluoro-2-pyridinyl)-oxy]-acetic acid or its 1-methylheptyl ester (FLUOROXYPYR); 5-(2-chloro-4-trifluoromethyl-phenoxy)-N-methylsulphonyl-2-nitrobenzamide (FOMESAFEN); N-phosphonomethyl-glycine (GLYPHOSATE); 2-{4-[(3-chloro-5-(trifluoromethyl)-2-pyridinyl)-oxy]phenoxy}-propanoic acid or its ethyl ester (HALOXYFOP); 3-cyclohexyl-6-dimethylamino-1-methyl-1,3,5-triazin-2,4-dione (HEXAZINONE); methyl 2-[4,5-dihydro-4-methyl-4-(1-methylethyl)-5-oxo-1H-imidazol-2-yl]-4(5)-methylbenzoate (IMAZAMETHABENZ); 2-(4,5-dihydro-4-methyl-4-isopropyl-5-oxo-1H-imidazol-2-yl)-pyridin-3-carboxylic acid (IMAZAPYR); 2-[5-methyl-5-(1-methylethyl)-4-oxo-2-imidazolin-2-yl]-3-quinolinecarboxylic acid (IMAZAQUIN); 2-[4,5-dihydro-4-methyl-4-isopropyl-5-oxo-(1H)-imidazol-2-yl]-5-ethyl-pyridine-3-carboxylic acid (IMAZETHAPYR); 3,5-diiodo-4-hydroxybenzonitrile (IOXYNIL); N,N-dimethyl-N'-(4-isopropylphenyl)-urea (ISOPROTURON); (2-ethoxy-1-methyl-2-oxo-ethyl)-5-[2-chloro-4-(trifluoromethyl)phenoxy]-2-nitrobenzoate (LACTOFEN); (2-methyl-4-chlorophenoxy)-acetic acid (MCPA); (4-chloro-2-methylphenoxy)propionic acid (MCPP); N-methyl-2-(1,3-benzothiazol-2-yloxy)-acetanilide (MEFENACET); 2-ethyl-6-methyl-N-(1-methyl-2-methoxyethyl)-chloroacetanilide (METOLACHLOR); N-(1-ethylpropyl)-3,4-dimethyl-2,6-dinitroaniline (PENDIMETHALIN); 4-amino-3,5,6-trichloropyridine-2-carboxylic acid (PICLORAM); 2-[1-(ethoxamino)-butylidene]-5-(2-ethylthiopropyl)-1,3-cyclohexadione (SETHOXYDIM); 2-chloro-4,6-bis-(ethylamino)-1,3,5-triazine (SIMAZIN); methyl 2-{[(4,6-dimethyl-2-pyrimidinyl)-aminocarbonyl-]aminosulphonyl}-benzoate (SULFOMETURON) and 2,6-dinitro-4-trifluoromethyl-N,N-dipropylaniline (TRIFLURALIN). Surprisingly, some mixtures also show a synergistic action.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.01 and 10 kg of active compound per hectare of soil surface, preferably between 0.05 and 5 kg per ha.

The preparation and use of the active compounds according to the invention can be seen from the following examples.

PREPARATION EXAMPLES

EXAMPLE 1 (IA-1)

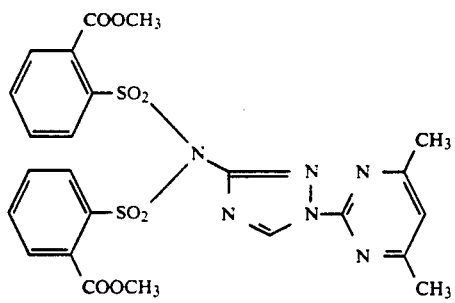

(Process (a))

26.1 g (0.1 mol) of methyl 2-chlorosulphonylbenzoate are added to a solution of 4.75 g (0.025 mol) of 1-(4,6-dimethyl-pyrimidin-2-yl)-3-amino-triazole in 100 ml of methylene chloride, the mixture is cooled to −5° C., and 11.2 g (0.1 mol) of diazabicyclo[2.2.2]octane, dissolved in 40 ml of methylene chloride, are added dropwise at −5° C. to 0° C. The reaction mixture is stirred for 2 days at room temperature (20° C.) and then washed with water; the methylene chloride phase is separated off, dried over sodium sulphate, filtered and concentrated. The oily residue can be crystallized using ethyl acetate.

The residue is filtered off with suction and dried, and 6.6 g (45% of theory) of 1-(4,6-dimethylpyrimidin-2-yl)-3-(N,N-bis-(2-methoxycarbonyl-phenylsulphonyl))-aminotriazole remain as colorless crystals of melting point 209°–212° C.

EXAMPLE 2 (IA-2)

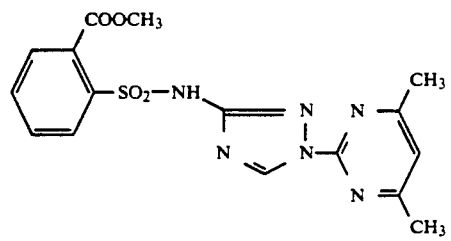

(Process (a))

1.17 g (0.002 mol) of 1-(4,6-dimethyl-pyrimidin-2-yl)-3-(N,N-bis-(2-methoxycarbonyl-phenylsulphonyl))aminotriazole are stirred at reflux temperature (about 70° C.) overnight in a mixture of 10 ml of 25% strength ammonia water and 10 ml of ethanol. In this process, the substance dissolves completely. The batch is concentrated and the residue is diluted with 30 ml of water. A pH of 3 is adjusted with hydrochloric acid and the product is filtered off with suction, washed and dried.

0.7 g (90% of theory) of 1-(4,6-dimethyl-pyrimidin-2-yl)-3-(2-methoxycarbonyl-phenylsulphonyl)aminotriazole in the form of colorless crystals of melting point 215° C.–217° C. is obtained.

The compounds of the formula (I), which is specified in more detail by formulae (IA), (IB) and (IC), which are listed in Table 2 below can be prepared in analogy to Examples 1 and 2 and following the general description of the process according to the invention:

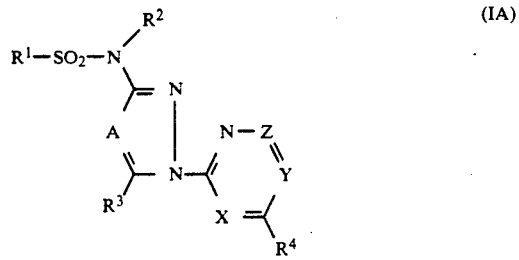

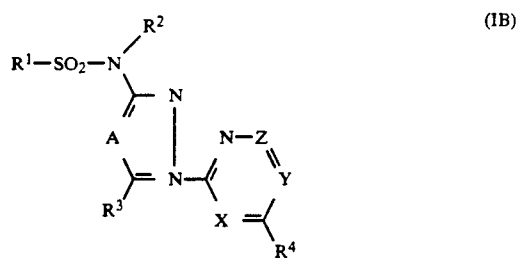

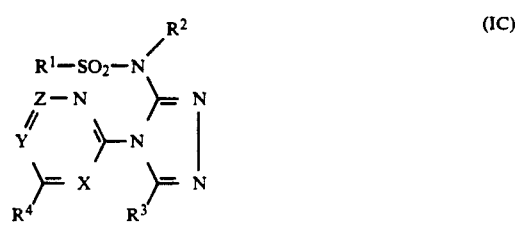

(In Table 6 below, A is indicated in each case instead of A′).

| Example No. | A | R¹ | R² | R³ | R⁴ | X | Y | Z | Melting Point (°C.) |
|---|---|---|---|---|---|---|---|---|---|
| IA-3 | N | 2-(COOCH₃)-phenyl | Na | H | CH₃ | N | CH | C—CH₃ | 111 |
| IA-4 | N | 2-(COOCH₃)-phenyl | K | H | CH₃ | N | CH | C—CH₃ | |
| IA-5 | N | 3-methyl-2-(COOCH₃)-thienyl | 3-(COOCH₃)-thien-2-yl-SO₂— | H | CH₃ | N | CH | C—CH₃ | 165 |
| IA-6 | N | 3-methyl-2-(COOCH₃)-thienyl | H | H | CH₃ | N | CH | C—CH₃ | 202 |
| IA-7 | N | 2-Cl-phenyl | 2-Cl-phenyl-SO₂— | H | CH₃ | N | CH | C—CH₃ | 229 |
| IA-8 | N | 2-Cl-phenyl | H | H | CH₃ | N | CH | C—CH₃ | 240 |
| IA-9 | N | 2-(COOC₃H₇)-benzyl (—CH₂—) | 2-(COOC₃H₇)-benzyl-SO₂— | H | CH₃ | N | CH | C—CH₃ | 152 |
| IA-10 | N | 2-(COOC₃H₇)-benzyl (—CH₂—) | H | H | CH₃ | N | CH | C—CH₃ | 190 |
| IB-11 | N | 2-(COOCH₃)-phenyl | H | H | CH₃ | N | CH | C—CH₃ | 204 |
| IA-12 | N | 2-(COOC₂H₅)-phenyl | 2-(COOC₂H₅)-phenyl-SO₂— | H | CH₃ | N | CH | C—CH₃ | |
| IA-13 | N | 2-(COOC₂H₅)-phenyl | H | H | CH₃ | N | CH | C—CH₃ | 89 |

-continued

| Example No. | A | R¹ | R² | R³ | R⁴ | X | Y | Z | Melting Point (°C.) |
|---|---|---|---|---|---|---|---|---|---|
| IA-14 | N | 2-F-phenyl | 2-F-phenyl-SO₂— | H | CH₃ | N | CH | C—CH₃ | 246 |
| IA-15 | N | 2-F-phenyl | H | H | CH₃ | N | CH | C—CH₃ | 269 |
| IA-16 | N | 2-Br-phenyl | 2-Br-phenyl-SO₂— | H | CH₃ | N | CH | C—CH₃ | |
| IA-17 | N | 2-Br-phenyl | H | H | CH₃ | N | CH | C—CH₃ | |
| IA-18 | N | 2-CF₃-phenyl | 2-CF₃-phenyl-SO₂— | H | CH₃ | N | CH | C—CH₃ | |
| IA-19 | N | 2-CF₃-phenyl | H | H | CH₃ | N | CH | C—CH₃ | |
| IA-20 | N | 2-OCHF₂-phenyl | 2-OCHF₂-phenyl-SO₂— | H | CH₃ | N | CH | C—CH₃ | |
| IA-21 | N | 2-OCHF₂-phenyl | 2-OCHF₂-phenyl-SO₂— | H | CH₃ | N | N | C—CH₃ | |
| IA-22 | N | 2-OCHF₂-phenyl | H | H | CH₃ | N | CH | C—CH₃ | 230 |
| IA-23 | N | 2-OCF₃-phenyl | 2-OCF₃-phenyl-SO₂— | H | CH₃ | N | CH | C—CH₃ | 202 |
| IA-24 | N | 2-SO₂CH₃-phenyl | 2-SO₂CH₃-phenyl-SO₂— | H | CH₃ | N | CH | C—CH₃ | |

-continued

| Example No. | A | R¹ | R² | R³ | R⁴ | X | Y | Z | Melting Point (°C.) |
|---|---|---|---|---|---|---|---|---|---|
| IA-25 | N | 2-OCF₃-phenyl | H | H | CH₃ | N | CH | C—CH₃ | 211 |
| IA-26 | N | 2-SO₂CH₃-phenyl | H | H | CH₃ | N | CH | C—CH₃ | |
| IA-27 | N | 2-SO₂N(CH₃)₂-phenyl | H | H | CH₃ | N | CH | C—CH₃ | 203 |
| IA-28 | N | 2-SCH₃-phenyl | H | H | CH₃ | N | CH | C—CH₃ | |
| IA-29 | N | 2-OCH₃-phenyl | H | H | CH₃ | N | CH | C—CH₃ | |
| IA-30 | N | 2-COOCH₃-phenyl | 2-COOCH₃-phenyl-SO₂— | H | CH₃ | N | CH | C—OCH₃ | |
| IA-31 | N | 2-COOCH₃-phenyl | H | H | CH₃ | N | CH | C—OCH₃ | 225 |
| IA-32 | N | 2-COOC₂H₅-phenyl | 2-COOC₂H₅-phenyl-SO₂— | H | CH₃ | N | CH | C—OCH₃ | 214 |
| IA-33 | N | 2-COOC₂H₅-phenyl | H | H | CH₃ | N | CH | C—OCH₃ | 167 |
| IA-34 | N | 3-methyl-2-COOCH₃-thienyl | 3-SO₂—-2-COOCH₃-thienyl | H | CH₃ | N | CH | C—OCH₃ | |
| IA-35 | N | 3-methyl-2-COOCH₃-thienyl | H | H | CH₃ | N | CH | C—OCH₃ | |

-continued

| Example No. | A | R¹ | R² | R³ | R⁴ | X | Y | Z | Melting Point (°C.) |
|---|---|---|---|---|---|---|---|---|---|
| IA-36 | N | 2-Cl-phenyl | H | H | $CH_3$ | N | CH | $C-OCH_3$ | |
| IA-37 | N | 2-F-phenyl | H | H | $CH_3$ | N | CH | $C-OCH_3$ | |
| IA-38 | N | 2-Cl-phenyl | 2-Cl-phenyl-$SO_2-$ | H | $CH_3$ | N | CH | $C-OCH_3$ | |
| IA-39 | N | 2-F-phenyl | 2-F-phenyl-$SO_2-$ | H | $CH_3$ | N | CH | $C-OCH_3$ | |
| IA-40 | N | 2-Br-phenyl | 2-Br-phenyl-$SO_2-$ | H | $CH_3$ | N | CH | $C-OCH_3$ | |
| IA-41 | N | 2-Br-phenyl | H | H | $CH_3$ | N | CH | $C-OCH_3$ | |
| IA-42 | N | 2-$CF_3$-phenyl | 2-$CF_3$-phenyl-$SO_2-$ | H | $CH_3$ | N | CH | $C-OCH_3$ | |
| IA-43 | N | 2-$CF_3$-phenyl | H | H | $CH_3$ | N | CH | $C-OCH_3$ | |
| IA-44 | N | 2-$OCHF_2$-phenyl | 2-$OCHF_2$-phenyl-$SO_2-$ | H | $CH_3$ | N | CH | $C-OCH_3$ | |
| IA-45 | N | 2-$OCHF_2$-phenyl | H | H | $CH_3$ | N | CH | $C-OCH_3$ | 223 |
| IA-46 | N | 2-$OCF_3$-phenyl | 2-$OCF_3$-phenyl-$SO_2-$ | H | $CH_3$ | N | CH | $C-OCH_3$ | |

-continued

| Example No. | A | R¹ | R² | R³ | R⁴ | X | Y | Z | Melting Point (°C.) |
|---|---|---|---|---|---|---|---|---|---|
| IA-47 | N | 2-(OCF₃)phenyl | H | H | CH₃ | N | CH | C—OCH₃ | 244 |
| IA-48 | N | 2-(SO₂CH₃)phenyl | H | H | CH₃ | N | CH | C—OCH₃ | |
| IA-49 | N | 2-(SO₂N(CH₃)₂)phenyl | H | H | CH₃ | N | CH | C—OCH₃ | 168 |
| IA-50 | N | 2-(SCH₃)phenyl | H | H | CH₃ | N | CH | C—OCH₃ | |
| IA-51 | N | 2-(COOCH₃)phenyl | 2-(COOCH₃)phenyl-SO₂— | H | OCH₃ | N | CH | C—OCH₃ | 208 |
| IA-52 | N | 2-(COOCH₃)phenyl | H | H | OCH₃ | N | CH | C—OCH₃ | 203 |
| IA-53 | N | 2-(COOC₂H₅)phenyl | 2-(COOC₂H₅)phenyl-SO₂— | H | OCH₃ | N | CH | C—OCH₃ | |
| IA-54 | N | 2-(COOC₂H₅)phenyl | H | H | OCH₃ | N | CH | C—OCH₃ | |
| IA-55 | N | 3-methyl-2-(COOCH₃)thienyl | 3-(SO₂—)-2-(COOCH₃)thienyl | H | OCH₃ | N | CH | C—OCH₃ | 195 |
| IA-56 | N | 3-methyl-2-(COOCH₃)thienyl | H | H | OCH₃ | N | CH | C—OCH₃ | |
| IA-57 | N | 2-Cl-phenyl | 2-Cl-phenyl-SO₂— | H | OCH₃ | N | CH | C—OCH₃ | |

-continued

| Example No. | A | R¹ | R² | R³ | R⁴ | X | Y | Z | Melting Point (°C.) |
|---|---|---|---|---|---|---|---|---|---|
| IA-58 | N | 2-Cl-phenyl | H | H | OCH₃ | N | CH | C—OCH₃ | |
| IA-59 | N | 2-F-phenyl | 2-F-phenyl-SO₂— | H | OCH₃ | N | CH | C—OCH₃ | |
| IA-60 | N | 2-F-phenyl | H | H | OCH₃ | N | CH | C—OCH₃ | |
| IA-61 | N | 2-Br-phenyl | 2-Br-phenyl-SO₂— | H | OCH₃ | N | CH | C—OCH₃ | |
| IA-62 | N | 2-Br-phenyl | H | H | OCH₃ | N | CH | C—OCH₃ | |
| IA-63 | N | 2-CF₃-phenyl | 2-CF₃-phenyl-SO₂— | H | OCH₃ | N | CH | C—OCH₃ | |
| IA-64 | N | 2-CF₃-phenyl | H | H | OCH₃ | N | CH | C—OCH₃ | |
| IA-65 | N | 2-OCHF₂-phenyl | 2-OCHF₂-phenyl-SO₂— | H | OCH₃ | H | CH | C—OCH₃ | |
| IA-66 | N | 2-OCHF₂-phenyl | H | H | OCH₃ | N | CH | C—OCH₃ | 194 |
| IA-67 | N | 2-OCF₃-phenyl | 2-OCF₃-phenyl-SO₂— | H | OCH₃ | N | CH | C—OCH₃ | 190 |
| IA-68 | N | 2-OCF₃-phenyl | H | H | OCH₃ | N | CH | C—OCH₃ | 233 |

-continued

| Example No. | A | R¹ | R² | R³ | R⁴ | X | Y | Z | Melting Point (°C.) |
|---|---|---|---|---|---|---|---|---|---|
| IA-69 | N | 2-(SO₂CH₃)-phenyl | H | H | OCH₃ | N | CH | C—OCH₃ | |
| IA-70 | N | 2-(SCH₃)-phenyl | H | H | OCH₃ | N | CH | C—OCH₃ | |
| IA-71 | N | 2-(SO₂N(CH₃)₂)-phenyl | H | H | OCH₃ | N | CH | C—OCH₃ | 203 |
| IA-72 | N | 2-(COOCH₃)-phenyl | 2-(COOCH₃)-phenyl-SO₂— | H | CF₃ | N | CH | C—OCH₃ | |
| IA-73 | N | 2-(COOCH₃)-phenyl | 2-(COOCH₃)-phenyl-SO₂— | H | OCH₃ | N | CH | C—Cl | |
| IA-74 | N | 2-(COOCH₃)-phenyl | H | H | CF₃ | N | CH | C—OCH₃ | |
| IA-75 | N | 2-(COOC₂H₅)-phenyl | 2-(COOC₂H₅)-phenyl-SO₂— | H | CF₃ | N | CH | C—OCH₃ | |
| IA-76 | N | 2-(COOC₂H₅)-phenyl | H | H | CF₃ | N | CH | C—OCH₃ | |
| IA-77 | N | 2-(OCF₃)-phenyl | H | H | CF₃ | N | CH | C—OCH₃ | |
| IA-78 | N | 2-(COOCH₃)-phenyl | H | H | OCH₃ | N | CH | C—Cl | |
| IA-79 | N | 2-(COOC₂H₅)-phenyl | 2-(COOC₂H₅)-phenyl-SO₂— | H | OCH₃ | N | CH | C—Cl | |

-continued

| Example No. | A | R¹ | R² | R³ | R⁴ | X | Y | Z | Melting Point (°C.) |
|---|---|---|---|---|---|---|---|---|---|
| IA-80 | N | 2-(COOC₂H₅)-phenyl | H | H | OCH₃ | N | CH | C—Cl | |
| IA-81 | N | 2-(OCHF₂)-phenyl | H | H | OCH₃ | N | CH | C—Cl | 226 |
| IA-82 | N | 2-(OCHF₂)-phenyl | 2-(OCHF₂)-phenyl-SO₂— | H | OCH₃ | N | CH | C—Cl | |
| IA-83 | N | 2-(OCF₃)-phenyl | 2-(OCF₃)-phenyl-SO₂— | H | OCH₃ | N | CH | C—Cl | |
| IA-84 | N | 2-(OCF₃)-phenyl | H | H | OCH₃ | N | CH | C—Cl | |
| IA-85 | N | 2-(COOCH₃)-phenyl | 2-(COOCH₃)-phenyl-SO₂— | H | OCH₃ | N | CH | C—OCHF₂ | |
| IA-86 | N | 2-(COOCH₃)-phenyl | H | H | OCH₃ | N | CH | C—OCHF₂ | |
| IA-87 | N | 2-(COOC₂H₅)-phenyl | 2-(COOC₂H₅)-phenyl-SO₂— | H | OCH₃ | N | CH | C—OCHF₂ | |
| IA-88 | N | 2-(COOC₂H₅)-phenyl | H | H | OCH₃ | N | CH | C—OCHF₂ | |
| IA-89 | N | 3-methyl-2-(COOCH₃)-thienyl | 3-(SO₂—)-2-(COOCH₃)-thienyl | H | OCH₃ | N | CH | C—OCHF₂ | |
| IA-90 | N | 3-methyl-2-(COOCH₃)-thienyl | H | H | OCH₃ | N | CH | C—OCHF₂ | |

-continued

| Example No. | A | R¹ | R² | R³ | R⁴ | X | Y | Z | Melting Point (°C.) |
|---|---|---|---|---|---|---|---|---|---|
| IA-91 | N | 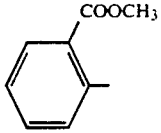 2-COOCH₃-phenyl | 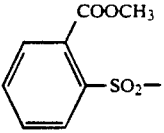 2-COOCH₃-phenyl-SO₂— | H | OCHF₂ | N | CH | C—OCHF₂ | |
| IA-92 | N | 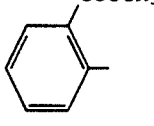 2-COOCH₃-phenyl | H | H | OCHF₂ | N | CH | C—OCHF₂ | |
| IA-93 | N | 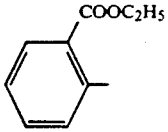 2-COOC₂H₅-phenyl | 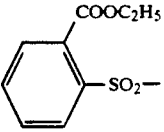 2-COOC₂H₅-phenyl-SO₂— | H | OCHF₂ | N | CH | C—OCHF₂ | |
| IA-94 | N | 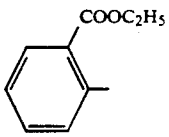 2-COOC₂H₅-phenyl | H | H | OCHF₂ | N | CH | C—OCHF₂ | |
| IA-95 | N | 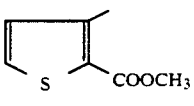 methyl 3-methylthiophene-2-carboxylate | 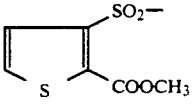 methyl 3-(SO₂—)thiophene-2-carboxylate | H | OCHF₂ | N | CH | C—OCHF₂ | |
| IA-96 | N | 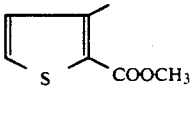 methyl 3-methylthiophene-2-carboxylate | H | H | OCHF₂ | N | CH | C—OCHF₂ | |
| IA-97 | N | 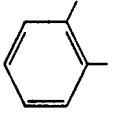 2-Cl-phenyl | 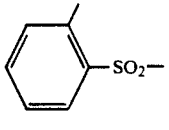 2-Cl-phenyl-SO₂— | H | OCHF₂ | N | CH | C—OCHF₂ | |
| IA-98 | N | 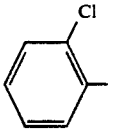 2-Cl-phenyl | H | H | OCHF₂ | N | CH | C—OCHF₂ | |
| IA-99 | N | 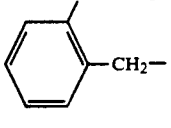 2-COOCH₃-benzyl | 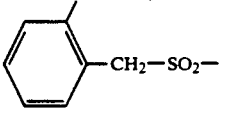 2-COOCH₃-benzyl-SO₂— | H | OCH₃ | N | CH | C—OCH₃ | |
| IA-100 | N | 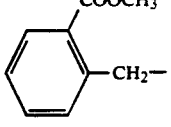 2-COOCH₃-benzyl | H | H | OCH₃ | N | CH | C—OCH₃ | |
| IA-101 | N | 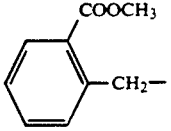 2-COOCH₃-benzyl | 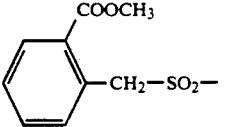 2-COOCH₃-benzyl-SO₂— | H | OCH₃ | N | CH | C—Cl | |

-continued

| Example No. | A | R¹ | R² | R³ | R⁴ | X | Y | Z | Melting Point (°C.) |
|---|---|---|---|---|---|---|---|---|---|
| IA-102 | N | 2-(COOCH₃)C₆H₄-CH₂- | H | H | OCH₃ | N | CH | C-Cl | |
| IA-103 | N | 2-(COOC₂H₅)C₆H₄-CH₂- | 2-(COOC₂H₅)C₆H₄-CH₂-SO₂- | H | OCH₃ | N | CH | C-OCH₃ | |
| IA-104 | N | 2-(COOC₂H₅)C₆H₄-CH₂- | H | H | OCH₃ | N | CH | C-OCH₃ | |
| IA-105 | N | 2-Cl-C₆H₄-CH₂- | 2-Cl-C₆H₄-CH₂-SO₂- | H | OCH₃ | N | CH | C-OCH₃ | |
| IA-106 | N | 2-Cl-C₆H₄-CH₂- | H | H | OCH₃ | N | CH | C-OCH₃ | |
| IA-107 | N | 2-Br-C₆H₄-CH₂- | 2-Br-C₆H₄-CH₂-SO₂- | H | OCH₃ | N | CH | C-OCH₃ | |
| IA-108 | N | 2-Br-C₆H₄-CH₂- | 2-Br-C₆H₄-CH₂-SO₂- | H | OCH₃ | N | CH | C-OCHF₂ | |
| IA-109 | N | 2-Br-C₆H₄-CH₂- | H | H | OCH₃ | N | CH | C-OCH₃ | |
| IA-110 | N | 2-(COOCH₃)C₆H₄-CH₂- | 2-(COOCH₃)C₆H₄-CH₂-SO₂- | H | OCH₃ | N | CH | C-OCHF₂ | |
| IA-111 | N | 2-(COOC₂H₅)C₆H₄-CH₂- | H | H | CH₃ | N | N | C-CH₃ | |
| IA-112 | N | 3-methyl-2-(COOCH₃)thien-yl- | 3-(SO₂-)-2-(COOCH₃)thienyl- | H | CH₃ | N | N | C-CH₃ | |

-continued

| Example No. | A | R¹ | R² | R³ | R⁴ | X | Y | Z | Melting Point (°C.) |
|---|---|---|---|---|---|---|---|---|---|
| IA-113 | N | 2-Cl-C₆H₄- | 2-Cl-C₆H₄-SO₂- | H | CH₃ | N | N | C—CH₃ | |
| IA-114 | N | 2-(COOCH₃)-C₆H₄- | 2-(COOCH₃)-C₆H₄-SO₂- | H | CH₃ | N | N | C—OCH₃ | |
| IA-115 | N | 2-(COOCH₃)-C₆H₄- | H | H | CH₃ | N | N | C—OCH₃ | |
| IA-116 | N | 2-(COOC₂H₅)-C₆H₄- | 2-(COOC₂H₅)-C₆H₄-SO₂- | H | CH₃ | N | N | C—OCH₃ | |
| IA-117 | N | 2-(COOC₂H₅)-C₆H₄- | H | H | CH₃ | N | N | C—OCH₃ | |
| IA-118 | N | 3-CH₃-2-(COOCH₃)-thienyl | 3-(SO₂-)-2-(COOCH₃)-thienyl | H | CH₃ | N | N | C—OCH₃ | |
| IA-119 | N | 3-CH₃-2-(COOCH₃)-thienyl | H | H | CH₃ | N | N | C—OCH₃ | |
| IA-120 | N | 2-Cl-C₆H₄- | Na | H | CH₃ | N | N | C—OCH₃ | |
| IA-121 | N | 2-Cl-C₆H₄- | 2-Cl-C₆H₄-SO₂- | H | CH₃ | N | N | C—OCH₃ | |
| IA-122 | N | 2-Cl-C₆H₄- | H | H | CH₃ | N | N | C—OCH₃ | |
| IA-123 | N | 2-(COOCH₃)-C₆H₄- | 2-(COOCH₃)-C₆H₄-SO₂- | H | OCH₃ | N | N | C—OCH₃ | 200 |

-continued

| Example No. | A | R¹ | R² | R³ | R⁴ | X | Y | Z | Melting Point (°C.) |
|---|---|---|---|---|---|---|---|---|---|
| IA-124 | N | 2-COOCH₃-phenyl | H | H | OCH₃ | N | N | C—OCH₃ | |
| IA-125 | N | 2-COOC₂H₅-phenyl | 2-COOC₂H₅-phenyl-SO₂— | H | OCH₃ | N | N | C—OCH₃ | |
| IA-126 | N | 2-COOC₂H₅-phenyl | H | H | OCH₃ | N | N | C—OCH₃ | |
| IA-127 | N | 3-COOCH₃-thien-2-yl | 3-COOCH₃-thien-2-yl-SO₂— | H | OCH₃ | N | N | C—OCH₃ | |
| IA-128 | N | 3-COOCH₃-thien-2-yl | H | H | OCH₃ | N | N | C—OCH₃ | |
| IA-129 | N | 2-Cl-phenyl | 2-Cl-phenyl-SO₂— | H | OCH₃ | N | N | C—OCH₃ | 184 |
| IA-130 | N | 2-Cl-phenyl | H | H | OCH₃ | N | N | C—OCH₃ | 225 |
| IA-131 | N | 2-F-phenyl | 2-F-phenyl-SO₂— | H | OCH₃ | N | N | C—OCH₃ | |
| IA-132 | N | 2-F-phenyl | H | H | OCH₃ | N | N | C—OCH₃ | |
| IA-133 | N | 2-Br-phenyl | 2-Br-phenyl-SO₂— | H | OCH₃ | N | N | C—OCH₃ | 232 |
| IA-134 | N | 2-Br-phenyl | H | H | OCH₃ | N | N | C—OCH₃ | |

-continued

| Example No. | A | R¹ | R² | R³ | R⁴ | X | Y | Z | Melting Point (°C.) |
|---|---|---|---|---|---|---|---|---|---|
| IA-135 | N | 2-CF₃-phenyl | 2-CF₃-phenyl-SO₂— | H | OCH₃ | N | N | C—OCH₃ | |
| IA-136 | N | 2-CF₃-phenyl | H | H | OCH₃ | N | N | C—OCH₃ | |
| IA-137 | N | 2-OCHF₂-phenyl | 2-OCHF₂-phenyl-SO₂— | H | OCH₃ | N | N | C—OCH₃ | 198 |
| IA-138 | N | 2-OCHF₂-phenyl | H | H | OCH₃ | N | N | C—OCH₃ | |
| IA-139 | N | 2-OCF₃-phenyl | 2-OCF₃-phenyl-SO₂— | H | OCH₃ | N | N | C—OCH₃ | 250 |
| IA-140 | N | 2-OCF₃-phenyl | H | H | OCH₃ | N | N | C—OCH₃ | 205 |
| IA-141 | N | 2-COOCH₃-benzyl (—CH₂—) | 2-COOCH₃-benzyl-SO₂— | H | OCHF₂ | N | CH | C—OCHF₂ | |
| IA-142 | N | 2-OCHF₂-benzyl (—CH₂—) | 2-OCHF₂-benzyl-SO₂— | H | OCH₃ | N | CH | C—OCH₃ | |
| IA-143 | N | 2-OCF₃-benzyl (—CH₂—) | 2-OCF₃-benzyl-SO₂— | H | OCH₃ | N | CH | C—OCH₃ | |
| IA-144 | N | 2-COOCH₃-phenyl | 2-COOCH₃-phenyl-SO₂— | H | CH₃ | N | N | C—CH₃ | |
| IA-145 | N | 2-COOCH₃-phenyl | H | H | CH₃ | N | N | C—CH₃ | |

-continued

| Example No. | A | R¹ | R² | R³ | R⁴ | X | Y | Z | Melting Point (°C.) |
|---|---|---|---|---|---|---|---|---|---|
| IA-146 | N | 2-(COOC₂H₅)-C₆H₄– | 2-(COOC₂H₅)-C₆H₄–SO₂– | H | CH₃ | N | N | C—CH₃ | |
| IA-147 | N | 2-(SCH₃)-C₆H₄– | 2-(SCH₃)-C₆H₄–SO₂– | H | OCH₃ | N | N | C—OCH₃ | |
| IA-148 | N | 2-(SO₂CH₃)-C₆H₄– | 2-(SO₂CH₃)-C₆H₄–SO₂– | H | OCH₃ | N | N | C—OCH₃ | |
| IA-149 | N | 2-(SO₂N(CH₃)₂)-C₆H₄– | 2-(SO₂N(CH₃)₂)-C₆H₄–SO₂– | H | OCH₃ | N | N | C—OCH₃ | |
| IA-150 | N | 2-(COOCH₃)-C₆H₄– | 2-(COOCH₃)-C₆H₄–SO₂– | H | OCH₃ | N | N | C—Cl | |
| IA-151 | N | 2-(COOCH₃)-C₆H₄– | 2-(COOCH₃)-C₆H₄–SO₂– | H | C₂H₅ | N | N | C—OCH₃ | |
| IA-152 | N | 2-(COOCH₃)-C₆H₄–CH₂– | 2-(COOCH₃)-C₆H₄–CH₂–SO₂– | H | OCH₃ | N | N | C—OCH₃ | |
| IA-153 | N | 2-(COOCH₃)-C₆H₄–CH₂– | H | H | OCH₃ | N | N | C—OCH₃ | |
| IA-154 | N | 2-(COOCH₃)-C₆H₄–CH₂– | H | H | OCH₃ | N | N | C—CH₃ | |
| IA-155 | N | 2-(COOCH₃)-C₆H₄– | 2-(COOCH₃)-C₆H₄–SO₂– | H | OCH₃ | N | N | C—NHC₂H₅ | |
| IA-156 | N | 2-(COOCH₃)-C₆H₄– | 2-(COOCH₃)-C₆H₄–SO₂– | H | OC₂H₅ | N | N | C—NHCH₃ | |

-continued

| Example No. | A | R¹ | R² | R³ | R⁴ | X | Y | Z | Melting Point (°C.) |
|---|---|---|---|---|---|---|---|---|---|
| IA-157 | N | 2-Cl-C₆H₄-CH₂- | 2-Cl-C₆H₄-CH₂-SO₂- | H | OCH₃ | N | N | C—OCH₃ | |
| IA-158 | N | 2-OCF₃-C₆H₄-CH₂- | 2-OCF₃-C₆H₄-CH₂-SO₂- | H | OCH₃ | N | N | C—OCH₃ | |
| IA-159 | N | 1-methyl-5-methyl-4-COOCH₃-pyrazol-3-yl | 1-methyl-5-SO₂-4-COOCH₃-pyrazol-3-yl | H | OCH₃ | N | CH | C—OCH₃ | |
| IA-160 | N | 1-methyl-5-methyl-4-COOCH₃-pyrazol-3-yl | H | H | OCH₃ | N | CH | C—OCH₃ | |
| IA-161 | N | 1-methyl-5-methyl-4-COOC₂H₅-pyrazol-3-yl | 1-methyl-5-SO₂-4-COOC₂H₅-pyrazol-3-yl | H | OCH₃ | N | CH | C—OCH₃ | |
| IA-162 | N | 1-methyl-5-methyl-4-COOC₂H₅-pyrazol-3-yl | H | H | OCH₃ | N | CH | C—OCH₃ | |
| IA-163 | N | 1-methyl-4-COOCH₃-pyrazol-3-yl | 1-methyl-5-SO₂-4-COOCH₃-pyrazol-3-yl | H | OCH₃ | N | N | C—OCH₃ | |
| IA-164 | N | 1-methyl-4-COOCH₃-pyrazol-3-yl | H | H | OCH₃ | N | N | C—OCH₃ | |
| IA-165 | N | 1-methyl-4-COOC₂H₅-pyrazol-3-yl | 1-methyl-5-SO₂-4-COOC₂H₅-pyrazol-3-yl | H | OCH₃ | N | N | C—OCH₃ | |
| IA-166 | N | 1-methyl-4-COOC₂H₅-pyrazol-3-yl | H | H | OCH₃ | N | N | C—OCH₃ | |

-continued

| Example No. | A | R¹ | R² | R³ | R⁴ | X | Y | Z | Melting Point (°C.) |
|---|---|---|---|---|---|---|---|---|---|
| IA-167 | N | 3-chloro-4-methylisothiazol-5-yl | 3-chloro-4-(SO₂—)isothiazol-5-yl | H | OCH₃ | N | N | C—OCH₃ | |
| IA-168 | N | 3-chloro-4-methylisothiazol-5-yl | 3-chloro-4-(SO₂—)isothiazol-5-yl | H | CH₃ | N | CH | C—CH₃ | 217 |
| IA-169 | N | 3-chloro-4-methylisothiazol-5-yl | H | H | CH₃ | N | CH | C—CH₃ | 252 |
| IA-170 | N | 4-chloro-2-(COOCH(CH₃)₂)phenyl | H | H | OCH₃ | N | N | C—OCH₃ | |
| IA-171 | N | 4-(OCHF₂)-2-(COOC₂H₅)phenyl | H | H | OCH₃ | N | CH | C—OCH₃ | |
| IA-172 | N | 3-(CF₃)pyridin-2-yl | H | H | OCH₃ | N | CH | C—OCH₃ | |
| IA-173 | N | 2-(C₆H₅)phenyl | H | H | OCH₃ | N | CH | C—OCH₃ | |
| IA-174 | N | 2-(C₆H₅)phenyl | H | H | OCH₃ | N | N | C—OCH₃ | |
| IA-175 | N | 2-(CH₃)phenyl | H | H | OCH₃ | N | N | C—OCH₃ | |
| IA-176 | N | 2-(SC₃H₇)phenyl | H | H | OCH₃ | N | N | C—OCH₃ | |
| IA-177 | N | 2-(SO₂—N(CH₃)(OCH₃))phenyl | H | H | OCH₃ | N | N | C—OCH₃ | |

-continued

| Example No. | A | R¹ | R² | R³ | R⁴ | X | Y | Z | Melting Point (°C.) |
|---|---|---|---|---|---|---|---|---|---|
| IA-178 | N | 2-OC₆H₅-phenyl | H | H | OCH₃ | N | N | C—OCH₃ | |
| IA-179 | N | 2-COOCH₃-phenyl | H | CH₃ | CH₃ | N | CH | C—CH₃ | 208 |
| IA-180 | N | 2-COOCH₃-phenyl | H | OCH₃ | CH₃ | N | CH | C—CH₃ | |
| IA-181 | N | 2-COOCH₃-phenyl | H | SCH₃ | CH₃ | N | CH | C—CH₃ | |
| IB-182 | N | 2-COOC₂H₅-phenyl | H | H | CH₃ | N | CH | C—CH₃ | |
| IB-183 | N | 2-COOCH₃-benzyl (—CH₂—) | H | H | OCH₃ | N | CH | C—OCH₃ | |
| IB-184 | H | 3-methyl-2-COOCH₃-thienyl | H | H | OCH₃ | N | N | C—OCH₃ | |
| IB-185 | N | 2-Cl-phenyl | H | H | CH₃ | N | N | C—OCH₃ | |
| IB-186 | N | 2-COOCH₃-phenyl | H | H | CH₃ | N | N | C—OCH₃ | |
| IB-187 | N | 2-COOCH₃-phenyl | H | H | OCH₃ | N | N | C—OCH₃ | |
| IB-188 | N | 2-COOC₂H₅-phenyl | H | H | OCH₃ | N | CH | C—Cl | |

-continued

| Example No. | A | R¹ | R² | R³ | R⁴ | X | Y | Z | Melting Point (°C.) |
|---|---|---|---|---|---|---|---|---|---|
| IB-189 | N | 2-C₆H₅-phenyl | H | H | OCH₃ | N | CH | C—OCH₃ | |
| IB-190 | N | 2-C₆H₅-phenyl | H | H | OCH₃ | N | N | C—OCH₃ | |
| IB-191 | N | 3-methyl-2-(COOCH₃)-thienyl | H | H | CH₃ | N | N | C—OCH₃ | |
| IC-192 | N | 4-(COOC₂H₅)-3-methyl-1-methyl-pyrazolyl | H | H | CH₃ | N | CH | C—CH₃ | 206 |
| IA-193 | N | 2-(COOCH₃)-phenyl | 2-(COOCH₃)-phenyl-SO₂— | H | OC₂H₅ | N | N | C—OC₂H₅ | 161 |
| IA-194 | N | 2-F-phenyl | 2-F-phenyl-SO₂— | H | OC₂H₅ | N | N | C—OC₂H₅ | 204 |
| IA-195 | N | 2-Br-phenyl | 2-Br-phenyl-SO₂— | H | OC₂H₅ | N | N | C—OC₂H₅ | 206 |
| IA-196 | N | 2-Br-phenyl | H | H | OC₂H₅ | N | N | C—OC₂H₅ | 190 |
| IA-197 | N | 2-OCF₃-phenyl | 2-OCF₃-phenyl-SO₂— | H | OC₂H₅ | N | N | C—OC₂H₅ | 134 |
| IA-198 | N | 3-methyl-2-(COOCH₃)-thienyl | 3-SO₂—-2-(COOCH₃)-thienyl | H | OC₂H₅ | N | N | C—OC₂H₅ | 160 |
| IA-199 | N | 2-Cl-phenyl | 2-Cl-phenyl-SO₂— | H | OC₂H₅ | N | N | C—OC₂H₅ | 237 |

-continued

| Example No. | A | R¹ | R² | R³ | R⁴ | X | Y | Z | Melting Point (°C.) |
|---|---|---|---|---|---|---|---|---|---|
| IA-200 | N | 2-Cl-C₆H₄ | 2-Cl-C₆H₄-SO₂— | H | OCH₃ | N | N | C—OC₂H₅ | 200 |
| IA-201 | N | 2-Cl-C₆H₄ | H | H | OCH₃ | N | N | C—OC₂H₅ | 189 |
| IA-202 | N | 2-COOCH₃-C₆H₄ | 2-COOCH₃-C₆H₄-CH₂— | H | OCH₃ | N | N | C—OC₂H₅ | 183 |
| IA-203 | N | 2-F-C₆H₄ | 2-F-C₆H₄-SO₂— | H | OCH₃ | N | N | C—OC₂H₅ | 190 |
| IA-204 | N | 2-F-C₆H₄ | H | H | OCH₃ | N | N | C—OC₂H₅ | 152 |
| IB-205 | N | 2-COOCH₃-C₆H₄ | 2-COOCH₃-C₆H₄-SO₂— | CH₃ | H | N | CH | CH | 155 |
| IB-206 | N | 2-COOCH₃-C₆H₄ | 2-COOCH₃-C₆H₄-SO₂— | CH₃ | CH₃ | N | CH | C—CH₃ | 195 |
| IB-207 | N | 2-COOCH₃-C₆H₄ | H | CH₃ | H | N | CH | CH | 185 |
| IB-208 | N | 2-COOCH₃-C₆H₄ | H | CH₃ | CH₃ | N | CH | C—CH₃ | 202 |
| IA-209 | CH | 2-COOCH₃-C₆H₄ | 2-COOCH₃-C₆H₄-SO₂— | H | CH₃ | N | CH | C—CH₃ | 177 |
| IA-210 | N | 2-COOCH₃-C₆H₄ | 2-COOCH₃-C₆H₄-SO₂— | H | H | N | CH | CH | 210 |

-continued

| Example No. | A | R¹ | R² | R³ | R⁴ | X | Y | Z | Melting Point (°C.) |
|---|---|---|---|---|---|---|---|---|---|
| IA-211 | N | 2-(COOCH₃)-phenyl | H | H | H | N | CH | CH | 213 |
| IA-212 | CH | 2-Cl-phenyl | 2-Cl-phenyl-SO₂— | H | CH₃ | N | CH | C—CH₃ | 340 |
| IA-213 | CH | 2-(COOCH₃)-phenyl | H | H | CH₃ | N | CH | C—CH₃ | 191 |
| IC-214 | N | 3-methyl-2-(COOCH₃)-thienyl | H | H | CH₃ | N | CH | C—CH₃ | 217 |
| IA-215 | N | 2,6-diCl-phenyl | 2,6-diCl-phenyl-SO₂— | H | CH₃ | N | CH | C—CH₃ | 195 |
| IA-216 | N | 2,6-diCl-phenyl | H | H | CH₃ | N | CH | C—CH₃ | 240 |
| IA-217 | N | 2-(COOCH₃)-phenyl | H | H | CH₃ | N | CH | C—CH₃ | 152 |
| IC-218 | N | 2-(COOCH₃)-phenyl-SO₂— | H | H | OCH₃ | N | CH | C—OCH₃ | 213 |
| IC-219 | N | 2-(OCF₃)-phenyl | H | H | OCH₃ | N | CH | C—OCH₃ | 225 |
| IC-220 | N | 2-(COOCH₃)-phenyl | H | H | OCH₃ | N | CH | C—OCH₃ | 210 |

-continued

| Example No. | A | R¹ | R² | R³ | R⁴ | X | Y | Z | Melting Point (°C.) |
|---|---|---|---|---|---|---|---|---|---|
| IC-221 | N | 2-(COOCH₃)C₆H₄-CH₂- | H | CH₃ | OCH₃ | N | CH | C—OCH₃ | 213 |
| IC-222 | N | 2-(SO₂NHOCH₃)C₆H₄- | H | H | OCH₃ | N | CH | C—OCH₃ | 215 |
| IA-223 | N | 2-(OCF₃)C₆H₄- | H | H | CH₃ | N | N | C—OCH₃ | 212 |
| IC-224 | N | 2-Cl-C₆H₄- | H | H | CH₃ | N | CH | C—OCH₃ | 139 |
| IA-225 | N | 2-(CF₃)C₆H₄- | 2-(CF₃)C₆H₄-SO₂- | H | OC₂H₅ | N | N | C—OC₂H₅ | |
| IA-226 | N | 2-(OCHF₂)C₆H₄- | 2-(OCHF₂)C₆H₄-SO₂- | H | OC₂H₅ | N | N | C—OC₂H₅ | 144 |
| IA-227 | N | 2-(SO₂CH₃)C₆H₄- | H | H | OC₂H₅ | N | N | C—OC₂H₅ | 192 |
| IA-228 | N | 2-(SO₂CH₃)C₆H₄- | 2-(SO₂CH₃)C₆H₄-SO₂- | H | OC₂H₅ | N | N | C—OC₂H₅ | 227 |
| IA-229 | N | 2-(CH₃)C₆H₄- | 2-(CH₃)C₆H₄-SO₂- | H | OC₂H₅ | N | N | C—OC₂H₅ | 205 |
| IA-230 | N | 2-(SO₂N(CH₃)₂)C₆H₄- | 2-(SO₂N(CH₃)₂)C₆H₄-SO₂- | H | OC₂H₅ | N | N | C—OC₂H₅ | 234 |
| IA-231 | N | 2-(OCHF₂)C₆H₄- | H | H | OC₂H₅ | N | N | C—OC₂H₅ | 162 |

-continued

| Example No. | A | R¹ | R² | R³ | R⁴ | X | Y | Z | Melting Point (°C.) |
|---|---|---|---|---|---|---|---|---|---|
| IA-232 | N | 2,3-dichlorophenyl | 2,3-dichlorophenyl-SO₂— | H | OC₂H₅ | N | N | C—OC₂H₅ | 203 |
| IA-233 | N | 2-(COOC₂H₅)phenyl | 2-(COOC₂H₅)phenyl-SO₂— | H | OC₂H₅ | N | N | C—OC₂H₅ | 72 |
| IA-234 | N | 2-fluorophenyl | 2-fluorophenyl-SO₂— | H | OCH₃ | N | N | C—OCH₃ | 228 |
| IA-235 | N | 2-SO₂N(C₂H₅)₂-phenyl | 2-SO₂N(C₂H₅)₂-phenyl-SO₂— | H | OC₂H₅ | N | N | C—OC₂H₅ | 180 |
| IA-236 | N | 2,4-dichlorophenyl | 2,4-dichlorophenyl-SO₂— | H | OC₂H₅ | N | N | C—OC₂H₅ | 170 |
| IA-237 | N | 2,4-dichlorophenyl | H | H | OC₂H₅ | N | N | C—OC₂H₅ | 215 |
| IA-238 | N | 2,4-difluorophenyl | 2,4-difluorophenyl-SO₂— | H | OC₂H₅ | N | N | C—OC₂H₅ | 188 |
| IA-239 | N | 2,4-dichlorophenyl | H | H | OC₂H₅ | N | N | C—OC₂H₅ | 210 |
| IA-240 | N | 2-methylphenyl | 2-methylphenyl-SO₂— | H | OCH₃ | N | N | C—OCH₃ | 219 |
| IA-241 | CH | 2-(CO—NH₂)phenyl | H | H | CH₃ | N | CH | C—CH₃ | 231 |

-continued

| Example No. | A | R¹ | R² | R³ | R⁴ | X | Y | Z | Melting Point (°C.) |
|---|---|---|---|---|---|---|---|---|---|
| IA-242 | N | 2-Cl-phenyl | H | H | $OC_2H_5$ | N | N | $C-OC_2H_5$ | 186 |
| IC-243 | N | ethyl 1,3-dimethyl-1H-pyrazole-4-carboxylate (1,5-dimethyl-4-COOC₂H₅-pyrazol-3-yl) | H | H | $CH_3$ | N | CH | $C-OCH_3$ | 190 |
| IA-244 | N | 2-Cl-6-CH₃-phenyl | H | H | $OCH_3$ | N | CH | $C-OCH_3$ | 275 |
| IA-245 | N | 2-Cl-phenyl | H | H | $OC_2H_5$ | N | N | $C-OC_2H_5$ | |
| IA-246 | N | 2-OCF₃-phenyl | H | H | $OC_2H_5$ | N | N | $C-OC_2H_5$ | |
| IA-247 | N | 2-SO₂N(CH₃)₂-phenyl | H | H | $OC_2H_5$ | N | N | $C-OC_2H_5$ | |
| IA-248 | N | 2-Br-phenyl | 2-Br-phenyl-SO₂— | H | $OCH_3$ | N | N | $C-OC_2H_5$ | |
| IA-249 | N | 2-OCHF₂-phenyl | 2-OCHF₂-phenyl-SO₂— | H | $OCH_3$ | N | N | $C-OC_2H_5$ | |
| IA-250 | N | 2-F-phenyl | H | H | $OC_2H_5$ | N | N | $C-OC_2H_5$ | |
| IA-251 | N | 2-SO₂N(C₂H₅)₂-phenyl | H | H | $OC_2H_5$ | N | N | $C-OC_2H_5$ | |

-continued

| Example No. | A | R¹ | R² | R³ | R⁴ | X | Y | Z | Melting Point (°C.) |
|---|---|---|---|---|---|---|---|---|---|
| IA-252 | N | 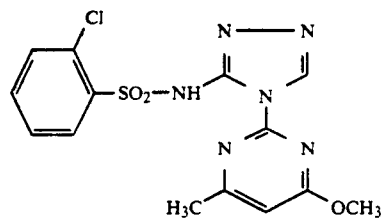 | H | H | CH₃ | N | CH | C—CH₃ | 192 |

The preparation of some more compounds according to the invention is described below with reference to examples.

Preparation of the compound mentioned in Table 6 as Example (IC-224)

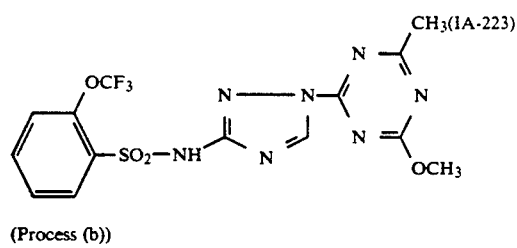

(Process (b))

3.0 g (0.025 mol) of dimethylformamide dimethyl acetal are added to a solution of 9.3 g ((0.025 mol) of N'-(4-methyl-6-methoxy-pyrimidin-2-yl)-N''-amino-N'''-(2-chlorophenylsulphonyl)-guanidine in 100 ml of methanol, and the reaction mixture is stirred for 2 hours at 20° C. During this process, the product is obtained in the form of crystals and is isolated by filtering off with suction.

8.0 g (84% of theory) of 4-(4-methyl-6-methoxypyrimidin-2-yl)-3-(2-chloro-phenylsulphonylamino)-triazole of melting point 139° C. are obtained.

Preparation of the compound mentioned in Table 6 as Example (IA-223):

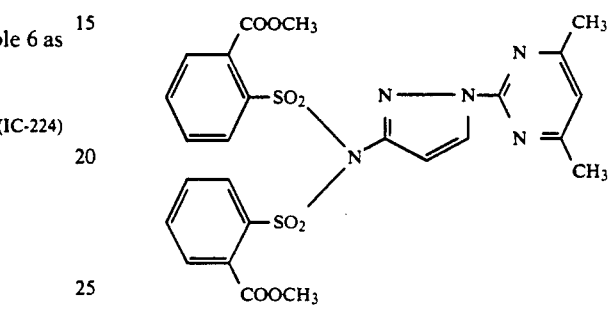

(Process (b))

2.7 g (0.023 mol) of dimethylformamide dimethyl acetal are added to a solution of 6.3 g (0.015 mol) of N'-(4-methyl-6-methoxy-s-triazin-2-yl-amino)-N'-(2-trifluoromethoxy-phenylsulphonyl)-guanidine in 20 ml of methanol, and the reaction mixture is refluxed to boiling point for 30 minutes. After cooling to room temperature (approximately 20° C.), the product is isolated by filtering off with suction and recrystallized from methanol.

4.5 g (70% of theory) of 1-(4-methyl-6-methoxy-s-triazin-2-yl)-3-(2-trifluoromethoxy-phenylsulphonylamino)triazole of melting point 212° C. are obtained.

Preparation of the compound listed in Table 6 as Example (IA-209):

20.2 g (0.18 mol) of 1,4-diazabicyclo-[2,2,2]-octane (DABCO) are added to a stirred mixture which has been cooled to 0° C. of 5.73 g (0.03 mol) of 1-(4,6-dimethylpyrimidin-2-yl)-3-amino-2-pyrazoline, 31.3 g (0.12 mol) of 2-methoxycarbonyl-benzenesulphonyl chloride and 200 ml of methylene chloride, and the reaction mixture is stirred for 18 hours at 20° C. under atmospheric pressure, with contact to atmospheric oxygen. The reaction solution is then washed with water and is dried over sodium sulphate. The mixture is filtered and evaporated, and the residue is crystallized using ethyl acetate. The crystalline product is isolated by filtering off with suction.

5.9 g (33% of theory) of 1-(4,6-dimethylpyrimidin-2-yl)-3-(N,N-bis-(2-methoxycarbonyl-phenylsulphonyl-)amino)-pyrazole of melting point 177° C. are obtained.

Preparation of the compound mentioned in Table 6 as Example (IA-242):

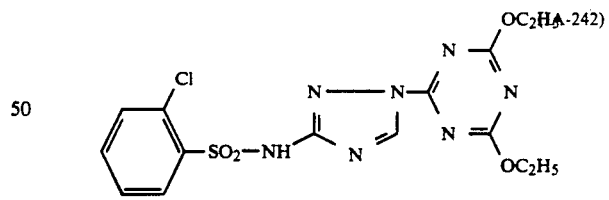

2.93 g (0.022 mol) of aluminum chloride are added at room temperature to a mixture of 5.02 g (0.02 mol) of 1-(4,6-diethoxy-s-triazin-2-yl)-3-amino-triazole and 60 ml of pyridine. This results in an exothermic reaction, and the temperature rises to above 40° C. After cooling to 10° C. to 20° C., 4.2 g (0.02 mol) of 2-chloro-benzenesulphonyl chloride are added to the stirred mixture, and the reaction mixture is then stirred for 4 hours at 50° C. After 12 more hours of stirring at 20° C., the mixture is stirred into 480 ml of 3N hydrochloric acid, the mixture is stirred for 30 minutes, filtered off with suction and washed with water. The crude product is recrystallized from ethanol.

6.1 g (72% of theory) of 1-(4,6-diethoxy-s-triazin-2-yl)-3-(2-chloro-phenylsulphonylamino)-triazole of melting point 186° C. are obtained.

Preparation of the dimethylammonium salt of the compound mentioned in Table 6 as Example (IA-130):

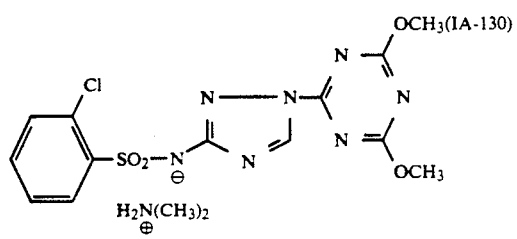

A mixture of 8.0 g (0.02 mol) of N'-(4,6-dimethoxy-s-triazin-2-yl-amino)-N''-(2-chloro-phenylsulphonyl)-guanidine, 4.5 g (0.0375 mol) of dimethylformamide dimethyl acetal and 30 ml of methanol is stirred for 10 minutes at 60° C. After stirring for one more hour at 20° C., the product obtained in the form of crystals is isolated by filtering off with suction.

4.6 g (52% of theory) of the dimethylammonium salt of 1-(4,6-dimethoxy-s-triazin-2-yl)-3-(2-chlorophenylsulphonylamino)-triazole of melting point 145° C. are obtained.

STARTING SUBSTANCES OF THE FORMULA (II)

EXAMPLE (II-1)

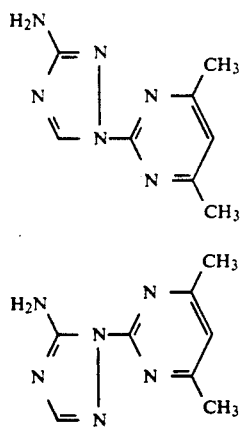

A mixture of 37.2 g (0.2 mol) of 2-methylsulphonyl-4,6-dimethyl-pyrimidine, 33.6 g (0.4 mol) of 3-amino-1,2,4-triazole, 27.6 g (0.2 mol) of potassium carbonate and 300 ml of acetonitrile is boiled to reflux for 3 hours. The mixture is then evaporated under a waterpump vacuum, the residue is stirred with 300 ml of water, a pH of 7 is adjusted with hydrochloric acid and the crystalline product is isolated by filtering off with suction. The resulting crude product is purified by chromatography over a silica gel column using methylene chloride/methanol (vol. 9:1) as the eluant. The solvent is carefully stripped off under a waterpump vacuum of each of the two eluate fractions obtained.

As the first fraction, 10.2 g (27% of theory) of 3-amino-1-(4,6-dimethyl-pyrimidin-2-yl)-1,2,4-triazole (IIA-1) of melting point 235° C.-238° C. are obtained 9.8 g (26% of theory) of 5-amino-1-(4,6-dimethyl-pyrimidin-2-yl)-1,2,4-triazole (IIB-1) of melting point 230° C.-232° C. are obtained as the second fraction.

EXAMPLE (II-2)

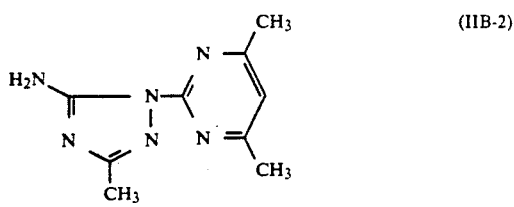

A mixture of 11.2 g (0.06 mol) of 4,6-dimethyl-2-methylsulphonyl-pyrimidine, 5.9 g (0.06 mol) of 3-amino-5-methyl-1,2,4-triazole, 8.3 g (0.06 mol) of potassium carbonate and 100 ml of acetonitrile is boiled to reflux for 5 hours. After evaporating, the residue is stirred into 100 ml of water, the product, which in this process is obtained in the form of crystals, is isolated by filtering off with suction, washed with water and recrystallized from acetonitrile.

4.6 g (37% of theory) of 1-(4,6-dimethylpyrimidin-2-yl)-5-amino-3-methyl-1,2,4-triazole of melting point 237° C. are obtained.

EXAMPLE (II-3)

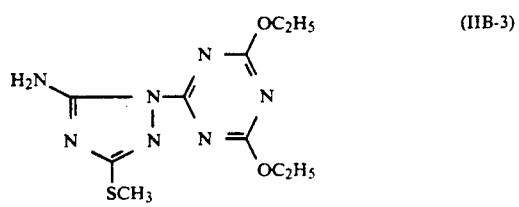

A mixture of 60 g (0.3 mol) of 4,6-diethoxy-2-hydrazino-s-triazine, 44 g (0.3 mol) of S,S-dimethyl cyanimino-dithiocarbonate and 300 ml of ethanol is boiled to reflux for 12 hours. After cooling to room temperature (approximately 20° C. ), the product which is obtained in the form of crystals is isolated by filtering off with suction.

73.8 g (83% of theory) of 1-(4,6-diethoxy-s-triazin-2-yl)-5-amino-3-methylthio-1,2,4-triazole of melting point 201° C. are obtained.

EXAMPLE (II-4)

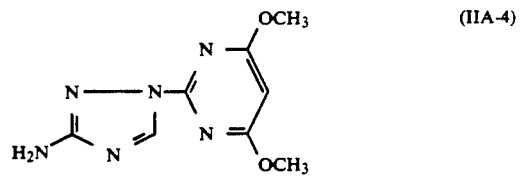

A mixture of 22.4 g (0.09 mol) of (4,6-dimethoxypyrimidin-2-yl-amino)-guanidine hydrochloride, 12.6 g (0.11 mol) of dimethylformamide dimethyl acetal and 150 ml of acetonitrile are boiled to reflux for 5 hours. After cooling to −10° C., the product obtained in the form of crystals is isolated by filtering off with suction.

10.9 g (54% of theory) of 1-(4,6-dimethoxypyrimidin-2-yl)-3-amino-1,2,4-triazole of melting point 219° C. are obtained.

The compounds of the formula (II), which is specified in more detail by formulae (IIA), (IIB) and (IIC), which are listed in Table 7 below can be prepared in analogy to Examples (II-1) to (II-4):

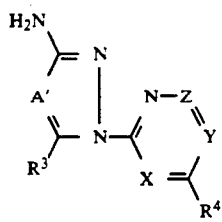

(IIA)

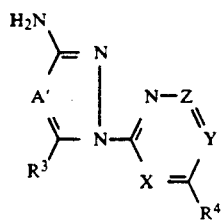

(IIB)

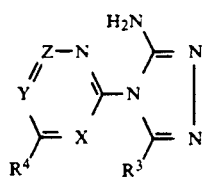

(IIC)

(In Table 7 below, A is indicated in each case instead of A').

TABLE 7

Examples of the compounds of the formula (II)

| Example No. | A | R³ | R⁴ | X | Y | Z | Melting Point (°C.) |
|---|---|---|---|---|---|---|---|
| IIB-5 | N | CH₃ | H | N | CH | CH | 223 |
| IIA-6 | N | CH₃ | CH₃ | N | CH | C—CH₃ | 211 |
| IIB-7 | N | SCH₃ | OCH₃ | N | CH | C—OCH₃ | 204 |
| IIB-8 | N | SCH₃ | CH₃ | N | CH | C—OCH₃ | 220 |
| IIB-9 | N | SCH₃ | OCH₃ | N | N | C—OC₂H₅ | 188 |
| IIB-10 | N | SCH₃ | OCH₃ | N | N | C—OCH₃ | 198 |
| IIA-11 | N | H | OCH₃ | N | N | C—OCH₃ | 233 |
| IIA-12 | N | H | OC₂H₅ | N | N | C—OC₂H₅ | 226 |
| IIA-13 | N | H | OCH₃ | N | N | C—OC₂H₅ | 211 |
| IIA-14 | N | H | H | N | H | C—H | 206 |
| IIB-15 | N | SCH₃ | H | N | CH | CH | 235 |
| IIB-16 | N | SO₂CH₃ | H | N | CH | CH | 276 |
| IIA-17 | N | H | CH₃ | N | CH | C—OCH₃ | 229 |

STARTING SUBSTANCES of the FORMULAE (IVA) and (IVB)

EXAMPLE (IV-1)

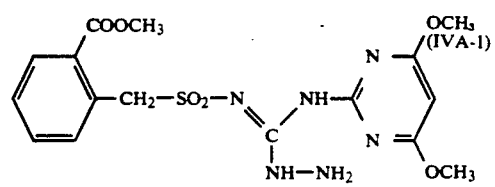

(IVA-1)

1.3 g (0.025 mol) of hydrazine hydrate are added, initially at 20° C., to a stirred suspension of 15.9 g (0.025 mol) of N'-(4,6-dimethoxy-pyrimidin-2-yl)-N"-methoxy-N"-(2-methoxycarbonyl-phenylsulphonyl)-N'''-(2-methoxycarbonyl-benzylsulphonyl)-guanidine in 100 ml of methanol, during which process the temperature of the reaction mixture rises to 30° C. and a clear solution is formed. The product which is separated in the form of crystals after four hours of stirring at 20° C. to 30° C. is isolated by filtering off with suction.

9.5 g (89% of theory) of N'-(4,6-dimethoxypyrimidin-2-yl)-N"-amino-N'''-(2-methoxycarbonyl-benzylsulphonyl)-guanidine of melting point 166° C. are obtained.

EXAMPLE (IV-2)

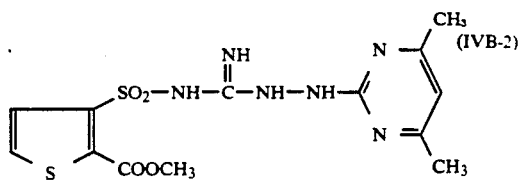

(IVB-2)

A solution of 3.8 g (0.01 mol) of N'-(4,6-dimethylpyrimidin-2-yl)-N"-amino-N'''-(2-methoxycarbonyl-thien-3-yl-sulphonyl)-guanidine in 100 ml of ethanol is boiled to reflux for 15 hours. After the reaction mixture has been cooled to 0° C., the product separated out in the form of crystals is isolated by filtering off with suction.

2.2 g (58% of theory) of N'-(4,6-dimethylpyrimidin-2-yl-amino)-N"-(2-methoxycarbonyl-thien-3-yl-sulphonyl)-guanidine of melting point 213° C. are obtained.

EXAMPLE (IV-3)

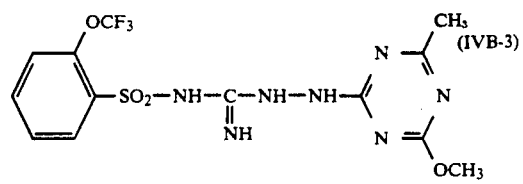

(IVB-3)

A mixture of 8.8 g (0.02 mol) of N'-(4-methyl-6-methoxy-s-triazin-2-yl)-N"-(2-trifluoromethoxy-phenyl-sulphonyl)-S-methyl-isothiourea, 1.0 g (0.02 mol) of hydrazine hydrate and 100 ml of ethanol is stirred for 60 minutes at 20° C. The product which during this process separates out in the form of crystals is isolated by filtering off with suction.

6.4 g (76% of theory) of (N'-(4-methyl-6-methoxy-s-triazin-2-yl-amino)-N"-(2-trifluoromethoxyphenylsulphonyl)-guanidine of melting point 245° C. are obtained.

The compounds, of the formulae (IVA) and (IVB), which are listed in Table 8 below can be prepared in analogy to Example (IV-1) to (IV-3):

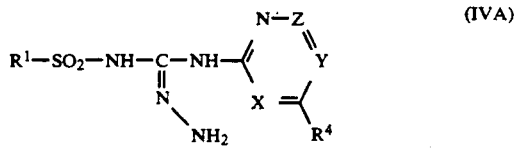

(IVA)

TABLE 8-continued

Examples of the compounds of the formula (IVA) and (IVB)

$$R^1-SO_2-NH-\underset{\underset{NH}{\|}}{C}-NH-\underset{\underset{R^4}{}}{\overset{N-Z}{\underset{Y}{\overset{\|}{C}}}}\quad \text{(IVB)}$$

| Example No. | R¹ | R⁴ | X | Y | Z | Melting Point (°C.) |
|---|---|---|---|---|---|---|
| IVA-4 | 2-(OCF₃)phenyl | OCH₃ | N | CH | C—OCH₃ | 134 |
| IVA-5 | 2-(COOCH₃)phenyl | OCH₃ | N | CH | C—OCH₃ | 159 |
| IVA-6 | 2-(OCHF₂)phenyl | CH₃ | N | CH | C—CH₃ | 98 |
| IVA-7 | 2-(OCF₃)phenyl | CH₃ | N | N | C—OCH₃ | amorphous |
| IVA-8 | 2-(OCF₃)phenyl | OCH₃ | N | N | C—OCH₃ | amorphous |
| IVA-9 | 2-Cl-phenyl | CH₃ | N | CH | C—OCH₃ | 166 |
| IVA-10 | 4-(COOC₂H₅)-3-methyl-1-methylpyrazol-5-yl | CH₃ | N | CH | C—CH₃ | 105 |
| IVA-11 | 4-(COOC₂H₅)-3-methyl-1-methylpyrazol-5-yl | CH₃ | N | N | C—CH₃ | 102 |
| IVB-12 | 2-(OCF₃)phenyl | OCH₃ | N | N | C—OCH₃ | 222 |
| IVB-13 | 2-Cl-phenyl | OCH₃ | N | N | C—OCH₃ | 138 |

TABLE 8-continued

Examples of the compounds of the formula (IVA) and (IVB)

| Example No. | R¹ | R⁴ | X | Y | Z | Melting Point (°C.) |
|---|---|---|---|---|---|---|
| IVB-14 | 2-(COOCH₃)phenyl | CH₃ | N | N | C—OCH₃ | 230 |
| IVB-15 | 2-Cl-phenyl | CH₃ | N | N | C—OCH₃ | 208 |
| IVB-16 | 2-Br-phenyl | CH₃ | N | N | C—OCH₃ | 195 |
| IVB-17 | 4-(COOC₂H₅)-1-methyl-3-methylpyrazol-5-yl | CH₃ | N | CH | C—OCH₃ | 262 |
| IVB-18 | 2-(COOCH₃)benzyl (—CH₂—) | OCH₃ | N | CH | C—OCH₃ | 195 |
| IVB-19 | 2-CF₃-phenyl | OCH₃ | N | N | C—OCH₃ | 215 |
| IVB-20 | 2-CF₃-phenyl | CH₃ | N | N | C—SCH₃ | 202 |
| IVB-21 | 2-OCH₃-phenyl | CH₃ | N | N | C—OCH₃ | 235 |
| IVB-22 | 2-OCHF₂-phenyl | OCH₃ | N | N | C—OCH₃ | 199 |

STARTING SUBSTANCES OF THE FORMULA (VI)

EXAMPLE (VI-1)

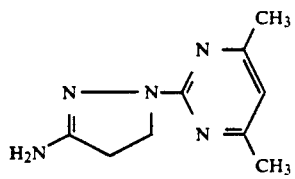

A solution, prepared from 0.6 g (0.026 mol) of sodium and 30 ml of ethanol, and 5.3 g (0.1 mol) of acrylonitrile are added in succession to a mixture of 13.8 g (0.1 mol) of 4,6-dimethyl-2-hydrazino-pyrimidine, 27 g (0.1 mol) of sodium methoxide and 80 ml of methanol. The reaction mixture is boiled to reflux for 18 hours and then evaporated. The residue is taken up in 200 ml of water, and this solution is brought to a pH of 6 using hydrochloric acid. 20 g of sodium chloride are then added, and the mixture is cooled to 10° C. The product which during this process separates out in the form of crystals is isolated by filtering off with suction.

10.8 g (57% of theory) of 1-(4,6-dimethyl-pyrimidin-2-yl)-3-amino-pyrazoline of melting point 205° C. are obtained.

STARTING SUBSTANCES OF THE FORMULA (IX)

EXAMPLE (IX-1)

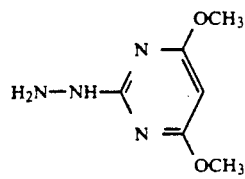

A mixture of 32.7 g (0.15 mol) of 4,6-dimethoxy-2-methylsulphonyl-pyrimidine, 7.3 g (0.15 mol) of hydrazine hydrate, 21 g (0.15 mol) of triethylamine and 200 ml of ethanol is stirred for 24 hours at 25° C. After the addition of a further 3.7 ml (0.076 mol) of hydrazine hydrate, the reaction mixture is stirred for a further 24 hours at 25° C. and then diluted with 200 ml of petroleum ether. The product which has been separated out in the form of crystals is isolated by filtering off with suction.

18.9 g (74% of theory) of 4,6-dimethoxy-2-hydrazino-pyrimidine of melting point 94° C. are obtained.

STARTING SUBSTANCES OF THE FORMULA (XIB)

EXAMPLE (XI-1)

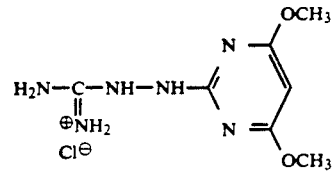

A mixture of 17.0 g (0.1 mol) of 4,6-dimethoxy-2-hydrazino-pyrimidine, 8.3 ml of concentrated hydrochloric acid, 4.2 g (0.1 mol) of cyanamide and 100 ml of ethanol is boiled to reflux for 18 hours. The mixture is then evaporated, the residue is crystallized using diethyl ether, and the crystalline product is isolated by filtering off with suction.

22.9 g (92% of theory) of (4,6-dimethoxy-pyrimidin-2-yl-amino)-guanidine hydrochloride of melting point 214° C. are obtained.

The compounds, of the formula (XIB), which are listed in Table 9 below can be prepared in analogy to Example (XI-1):

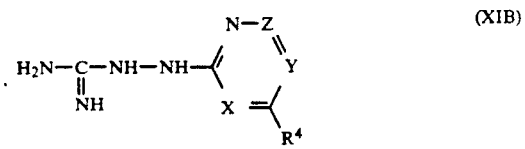

TABLE 9
Examples of the compounds of the formula (XIB)

| Example No. | $R^4$ | X | Y | Z | Melting Point (°C.) |
|---|---|---|---|---|---|
| XIB-2 | CH$_3$ | N | CH | C—CH$_3$ | 218 |
| XIB-3 | OCH$_3$ | N | CH | C—Cl | 237 |
| XIB-4 | OC$_2$H$_5$ | N | N | C—OC$_2$H$_5$ | 169 |
| XIB-5 | OCH$_3$ | N | N | C—OCH$_3$ | 235 |
| XIB-6 | OCH$_3$ | N | N | C—OC$_2$H$_5$ | 220 |

USE EXAMPLES

EXAMPLE A

Pre-emergence test

Solvent: 5 parts by weight of acetone
Emulsifier: 1 part by weight of alkylaryl polyglycol ether.

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)
100% = total destruction.

In this test, for example, the compounds according to Preparation Examples (IA-2), (IA-3), (IA-6), (IA-8) and (IA-223) show a clearly superior activity compared with the prior art. This applies in particular also to the compounds according to Preparation Examples (IA-25) and (IA-68).

EXAMPLE B

Post-emergence test

Solvent: 5 parts by weight of acetone
Emulsifier: 1 part by weight of alkylaryl polyglycol ether.

To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:

0% = no action (like untreated control)
100% = total destruction.

In this test, for example, the compounds according to Preparation Examples (IA-1), (IA-2), (IA-5), (IA-6), (IA-8), (IA-52) and (IA-3) show a clearly superior activity compared with the prior art. This also applies to the compounds according to the Preparation Examples (IA-25) and (IA-68).

It will be appreciated that the instant specification and claims are set forth by way of illustration and not limitation, and that various modifications and changes may be made without departing from the spirit and scope of the present invention.

What is claimed is:

1. A compound of the formula

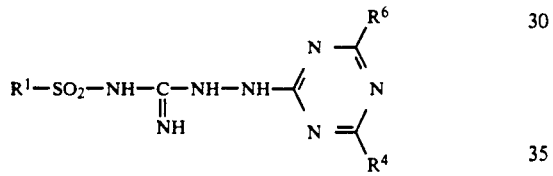

in which
R$^1$ stands for the radical

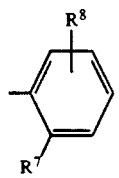

wherein
R$^7$ and R$^8$ are identical or different and stand for hydrogen, fluorine, chlorine, bromine, iodine, cyano, nitro, C$_1$–C$_6$-alkyl (which is optionally substituted by fluorine, chlorine, bromine, cyano, carboxyl, C$_1$–C$_4$-alkoxycarbonyl, C$_1$–C$_4$-alkylamino-carbonyl, di-(C$_1$–C$_4$-alkyl)aminocarbonyl, hydroxyl, C$_1$–C$_4$-alkoxy, formyloxy, C$_1$–C$_4$-alkyl-carbonyloxy, C$_1$–C$_4$-alkoxycarbonyloxy, C$_1$–C$_4$-alkylamino-carbonyloxy, C$_1$–C$_4$-alkylthio, C$_1$–C$_4$-alkylsulphinyl, C$_1$–C$_4$-alkylsulphonyl, di-(C$_1$–C$_4$-alkyl)-aminosulphonyl, C$_3$–C$_6$-cycloalkyl or phenyl), for C$_2$–C$_6$-alkenyl (which is optionally substituted by fluorine, chlorine, bromine, cyano, C$_1$–C$_4$-alkoxycarbonyl, carboxyl or phenyl), for C$_2$–C$_6$-alkinyl (which is optionally substituted by fluorine, chlorine, bromine, cyano, C$_1$–C$_4$-alkoxycarbonyl, carboxyl or phenyl), for C$_1$–C$_4$-alkoxy (which is optionally substituted by fluorine, chlorine, bromine, cyano, carboxyl, C$_1$–C$_4$-alkoxycarbonyl, C$_1$–C$_4$-alkoxy, C$_1$–C$_4$-alkylthio, C$_1$–C$_4$-alkylsulphinyl or C$_1$–C$_4$-alkylsulphonyl), for C$_1$–C$_4$-alkylthio (which is optionally substituted by fluorine, chlorine, bromine, cyano, carboxyl, C$_1$–C$_4$-alkoxy-carbonyl, C$_1$–C$_4$-alkylthio, C$_1$–C$_4$-alkylsulphinyl or C$_1$–C$_4$-alkylsulphonyl), for C$_3$–C$_6$-alkenyloxy (which is optionally substituted by fluorine, chlorine, bromine, cyano or C$_1$–C$_4$-alkoxycarbonyl), for C$_2$–C$_6$-alkenylthio (which is optionally substituted by fluorine, chlorine, bromine, cyano, nitro, C$_1$–C$_3$-alkylthio or C$_1$–C$_4$-alkoxycarbonyl), C$_3$–C$_6$-alkinyloxy, C$_3$–C$_6$-alkinylthio or for the radical —S(O)$_p$—R$^9$, p standing for the numbers 1 or 2 and R$^9$ standing for C$_1$–C$_4$-alkyl (which is optionally substituted by fluorine, chlorine, bromine, cyano or C$_1$–C$_4$-alkoxy-carbonyl), C$_3$–C$_6$-alkenyl, C$_3$–C$_6$-alkinyl, C$_1$–C$_4$-alkoxy, C$_1$–C$_4$-alkoxy-C$_1$–C$_4$-alkylamino, C$_1$–C$_4$-alkylamino, di-(C$_1$–C$_4$-alkyl)-amino or for the radical —N-HOR$^{10}$, R$^{10}$ standing for C$_1$–C$_6$-alkyl (which is optionally substituted by fluorine, chlorine, cyano, C$_1$–C$_4$-alkoxy, C$_1$–C$_4$-alkylthio, C$_1$–C$_4$-alkylsulphinyl, C$_1$–C$_4$-alkylsulphonyl, C$_1$–C$_4$-alkyl-carbonyl, C$_1$–C$_4$-alkoxy-carbonyl, C$_1$–C$_4$-alkylamino-carbonyl or di-(C$_1$–C$_4$-alkyl)-aminocarbonyl), for C$_3$–C$_6$-alkenyl (which is optionally substituted by fluorine, chlorine or bromine), C$_3$–C$_6$-alkinyl, C$_3$–C$_6$-cycloalkyl, C$_3$–C$_6$-cycloalkyl-C$_1$–C$_2$-alkyl, phenyl-C$_1$–C$_2$-alkyl (which is optionally substituted by fluorine, chlorine, nitro, cyano, C$_1$–C$_4$-alkyl, C$_1$–C$_4$-alkoxy or C$_1$–C$_4$-alkoxy-carbonyl), for benzhydryl or for phenyl (which is optionally substituted by fluorine, chlorine, nitro, cyano, C$_1$–C$_4$-alkyl, trifluoromethyl, C$_1$–C$_4$-alkoxy, C$_1$–C$_2$-fluoroalkoxy, C$_1$–C$_4$-alkylthio, trifluoromethylthio or C$_1$–C$_4$-alkoxy-carbonyl), R$^7$ and R$^8$ furthermore stand for phenyl or phenoxy, for C$_1$–C$_4$-alkylcarbonylamino, C$_1$–C$_4$-alkoxycarbonylamino, C$_1$–C$_4$-alkylamino-carbonylamino, di-(C$_1$–C$_4$-alkyl)-amino-carbonylamino, or for the radical —CO—R$^{11}$, R$^{11}$ standing for C$_1$–C$_6$-alkyl, C$_1$–C$_6$-alkoxy, C$_3$–C$_6$-cycloalkoxy, C$_3$–C$_6$-alkenyloxy, C$_1$–C$_4$-alkylthio, amino, C$_1$–C$_4$-alkylamino, C$_1$–C$_4$-alkoxyamino, C$_1$–C$_4$-alkoxy-C$_1$–C$_4$-alkyl-amino or di-(C$_1$–C$_4$-alkyl)-amino (which are optionally substituted by fluorine and/or chlorine), R$^7$ and R$^8$ furthermore stand for C$_1$–C$_4$-alkylsulphonyloxy, di-(C$_1$–C$_4$-alkyl)-aminosulphonylamino or for the radical —CH=N—R$^{12}$, R$^{12}$ standing for C$_1$–C$_6$-alkyl which is optionally substituted by fluorine, chlorine, cyano, carboxyl, C$_1$–C$_4$-alkoxy, C$_1$–C$_4$-alkylthio, C$_1$–C$_4$-alkylsulphinyl or C$_1$–C$_4$-alkylsulphonyl, for benzyl which is optionally substituted by fluorine or chlorine, for C$_3$–C$_6$-alkenyl or C$_3$–C$_6$-alkinyl, each of which is optionally-substituted by fluorine or chlorine, for phenyl which is optionally substituted by fluorine, chlorine, bromine, C$_1$–C$_4$-alkyl, C$_1$–C$_4$-alkoxy, trifluoromethyl, trifluoromethoxy or trifluoromethylthio, for C$_1$–C$_6$-alkoxy, C$_3$–C$_6$-alkenoxy, C$_3$–C$_6$-alkinoxy or benzyloxy, each of which is optionally substituted by fluorine and/or chlorine, for amino, $C_1$-$C_4$-alkylamino, chlorine, for amino, $C_1$-$C_4$-alkylamino, di-($C_1$-$C_4$-alkyl)-amino, phenylamino, $C_1$-$C_4$-alkyl-carbonylamino, $C_1$-$C_4$-alkoxy-carbonyl-amino, phenylsulphonylamino which is optionally substituted by fluorine, chlorine, bromine or methyl, wherein furthermore $R^1$ stands for the radical

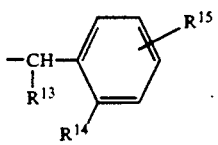

wherein $R^{13}$ stands for hydrogen or $C_1$-$C_4$-alkyl, $R^{14}$ and $R^{15}$ are identical or different and stand for hydrogen, fluorine, chlorine, bromine, nitro, cyano, $C_1$-$C_4$-alkyl (which is optionally substituted by fluorine and/or chlorine), $C_1$-$C_4$-alkoxy (which is optionally substituted by fluorine and/or chlorine), carboxyl, $C_1$-$C_4$-alkoxy-carbonyl, $C_1$-$C_4$-alkylsulphonyl or di-($C_1$-$C_4$-alkyl)aminosulphonyl;

wherein furthermore $R^1$ stands for the radical

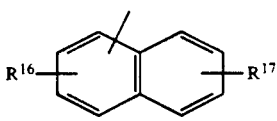

wherein $R^{16}$ and $R^{17}$ are identical or different and stand for hydrogen, fluorine, chlorine, bromine, nitro, cyano, $C_1$-$C_4$-alkyl (which is optionally substituted by fluorine and/or chlorine) or $C_1$-$C_4$-alkoxy (which is optionally substituted by fluorine and/or chlorine);

wherein furthermore $R^1$ stands for the radical

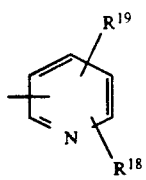

wherein $R^{18}$ and $R^{19}$ are identical or different and stand for hydrogen, fluorine, chlorine, bromine, nitro, cyano, $C_1$-$C_4$-alkyl (which is optionally substituted by fluorine and/or chlorine), $C_2$-$C_4$-alkenyl (which is optionally substituted by fluorine and/or chlorine), $C_1$-$C_4$-alkoxy (which is optionally substituted by fluorine and/or chlorine), for $C_1$-$C_4$-alkylthio, $C_1$-$C_4$-alkylsulphinyl or $C_1$-$C_4$-alkylsulphonyl (which are optionally substituted by fluorine and/or chlorine), and for di-($C_1$-$C_4$-alkyl)aminosulphonyl, $C_1$-$C_4$-alkoxy-carbonyl, dimethylaminocarbonyl or dioxolanyl;

wherein furthermore $R^1$ stands for the radical

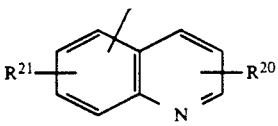

wherein $R^{20}$ and $R^{21}$ are identical or different and stand for hydrogen, fluorine, chlorine, bromine, $C_1$-$C_4$-alkyl (which is optionally substituted by fluorine and/or bromine), $C_1$-$C_4$-alkoxy (which is optionally substituted by fluorine and/or chlorine), for $C_1$-$C_4$-alkylthio, $C_1$-$C_4$-alkylsulphinyl or $C_1$-$C_4$-alkylsulphonyl (which are optionally substituted by fluorine and/or chlorine), or for di-($C_1$-$C_4$-alkyl)-aminosulphonyl;

wherein furthermore $R^1$ stands for the radical

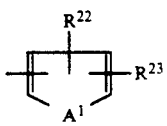

wherein $R^{22}$ and $R^{23}$ are identical or different and stand for hydrogen, fluorine, chlorine, bromine, cyano, nitro, $C_1$-$C_4$-alkyl (which is optionally substituted by fluorine, chlorine, $C_1$-$C_4$-alkoxy and/or $C_1$-$C_4$-halogenoalkoxy), $C_1$-$C_4$-alkoxy (which is optionally substituted by fluorine and/or chlorine), $C_1$-$C_4$-alkylthio, $C_1$-$C_4$-alkylsulphinyl or $C_1$-$C_4$-alkylsulphonyl (which is optionally substituted by fluorine and/or chlorine), di-($C_1$-$C_4$-alkyl)-amino-sulphonyl or $C_1$-$C_4$-alkoxycarbonyl, and $A^1$ stands for oxygen, sulphur or the grouping N—$Z^1$, $Z^1$ standing for hydrogen, $C_1$-$C_4$-alkyl (which is optionally substituted by fluorine, chlorine, bromine or cyano), $C_3$-$C_6$-cycloalkyl, benzyl, phenyl (which is optionally substituted by fluorine, chlorine, bromine or nitro), $C_1$-$C_4$-alkyl-carbonyl, $C_1$-$C_4$-alkoxy-carbonyl or di-($C_1$-$C_4$-alkyl)-aminocarbonyl;

wherein furthermore $R^1$ stands for the radical

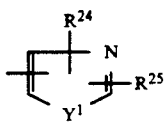

wherein $R^{24}$ and $R^{25}$ are identical or different and stand for hydrogen, $C_1$-$C_4$-alkyl, halogen, $C_1$-$C_4$-alkoxycarbonyl, $C_1$-$C_4$-alkoxy or $C_1$-$C_4$halogenoalkoxy, $Y^1$ stands for sulphur or the grouping N-$R^{26}$, $R^{26}$ standing for hydrogen or $C_1$-$C_4$-alkyl;

wherein furthermore $R^1$ stands for the radical

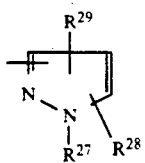

wherein
R²⁷ stands for hydrogen, $C_1$-$C_4$-alkyl, phenyl or (iso)quinolinyl,
R²⁸ stands for hydrogen, halogen, cyano, nitro, $C_1$-$C_4$-alkyl (which is optionally substituted by fluorine and/or chlorine), $C_1$-$C_4$-alkoxy (which is optionally substituted by fluorine and/or chlorine), dioxolanyl or $C_1$-$C_4$-alkoxy-carbonyl and
R²⁹ stands for hydrogen, halogen or $C_1$-$C_4$-alkyl;

wherein furthermore
R¹ stands for the radical

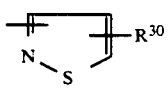

wherein
R³⁰ stands for halogen, $C_1$-$C_4$-alkyl or $C_1$-$C_4$-alkoxy-carbonyl;

wherein furthermore
R¹ stands for the radical

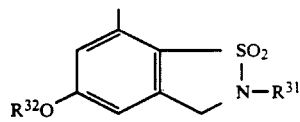

wherein
R³¹ stands for $C_1$-$C_4$-alkyl and
R³² stands for $C_1$-$C_4$-alkyl, wherein furthermore
R¹ stands for the radical

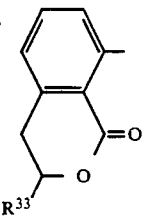

wherein
R³³ stands for hydrogen or methyl;
R⁴ stands for hydrogen, fluorine, chlorine, bromine, $C_1$-$C_4$-alkyl, $C_1$-$C_4$-halogenoalkyl, $C_1$-$C_2$-alkoxy-$C_1$-$C_2$-alkyl, $C_1$-$C_4$-alkoxy, $C_1$-$C_4$-halogenoalkoxy, $C_1$-$C_4$-alkylthio, $C_1$-$C_4$-halogenoalkylthio, amino, $C_1$-$C_4$-alkylamino, dimethylamino or diethylamino,
R⁶ stands for hydrogen, fluorine, chlorine, bromine, $C_1$-$C_4$-alkyl, $C_1$-$C_4$-halogenoalkyl, $C_1$-$C_4$-alkoxy, $C_1$-$C_4$-halogenoalkoxy, $C_1$-$C_4$-alkylthio, $C_1$-$C_4$-alkyl-amino, dimethylamino or diethylamino.

* * * * *

UNITED STATES PATENT AND TRADEMARK OFFICE
CERTIFICATE OF CORRECTION

PATENT NO. : 5,091,529
DATED : February 25, 1992
INVENTOR(S) : Kirsten et al.

It is certified that error appears in the above-identified patent and that said Letters Patent is hereby corrected as shown below:

Col. 121, lines 1-2   Delete " chlorine for amino, $C_1$-$C_4$-alkylamino, "

Col. 121, line 4   Before " phenylsulphonylamino " insert --$C_1$-$C_4$-alkyl-sulphonylamino or for--.

Col. 122, lines 63 64   Delete " $C_1$-$C_4$halogenoalkoxy " and substitute -- $C_1$-$C_4$-halogenoalkoxy --

Signed and Sealed this

Tenth Day of May, 1994

Attest:

BRUCE LEHMAN

*Attesting Officer*   *Commissioner of Patents and Trademarks*